(12) United States Patent
Marchand et al.

(10) Patent No.: US 8,568,472 B2
(45) Date of Patent: Oct. 29, 2013

(54) INTEGRATED HEART VALVE DELIVERY SYSTEM

(75) Inventors: Philippe Marchand, Lake Forest, CA (US); David M. Taylor, Lake Forest, CA (US); Robert Milich, Jr., Long Beach, CA (US); David J. Evans, Irvine, CA (US); Christopher Chia, Irvine, CA (US); Ronaldo C. Cayabyab, Mission Viejo, CA (US); Robert Royal Bowes, Laguna Hills, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1002 days.

(21) Appl. No.: 11/852,977

(22) Filed: Sep. 10, 2007

(65) Prior Publication Data

US 2008/0065011 A1  Mar. 13, 2008

Related U.S. Application Data

(60) Provisional application No. 60/843,470, filed on Sep. 8, 2006.

(51) Int. Cl.
*A61F 2/06* (2013.01)
(52) U.S. Cl.
USPC .......................................... 623/2.11; 623/1.11
(58) Field of Classification Search
USPC .......... 623/2.11, 2.1, 1.1, 1.11, 1.12; 606/108
See application file for complete search history.

(56) References Cited

U.S. PATENT DOCUMENTS

| | | |
|---|---|---|
| 3,409,013 A | 11/1968 | Berry |
| 3,587,115 A | 6/1971 | Shiley |
| 3,671,979 A | 6/1972 | Moulopoulos |
| 4,056,854 A | 11/1977 | Boretos et al. |
| 4,592,340 A | 6/1986 | Boyles |
| 4,733,665 A | 3/1988 | Palmaz |
| 4,777,951 A | 10/1988 | Cribier et al. |
| 4,787,899 A | 11/1988 | Lazarus |
| 4,796,629 A | 1/1989 | Grayzel |
| 5,059,177 A | 10/1991 | Towne et al. |
| 5,085,635 A | 2/1992 | Cragg |
| 5,089,015 A | 2/1992 | Ross |
| 5,167,628 A | 12/1992 | Boyles |
| 5,190,050 A * | 3/1993 | Nitzsche ........................ 600/585 |
| 5,332,402 A | 7/1994 | Teitelbaum |
| 5,370,685 A | 12/1994 | Stevens |

(Continued)

FOREIGN PATENT DOCUMENTS

| | | |
|---|---|---|
| CA | 2 595 233 | 7/2006 |
| WO | WO 99/12483 | 3/1999 |

(Continued)

OTHER PUBLICATIONS

International Search Report for PCT/US2007/078053 dated Feb. 15, 2008.

(Continued)

*Primary Examiner* — Gregory Anderson
(74) *Attorney, Agent, or Firm* — David L. Hauser

(57) ABSTRACT

Embodiments of the present disclosure provide a delivery apparatus for delivering a prosthetic heart valve to a native valve site via the human vasculature. The delivery apparatus is particularly well-suited for advancing a prosthetic valve through the aorta (i.e., in a retrograde approach) for replacing a stenotic aortic valve.

23 Claims, 24 Drawing Sheets

(56) References Cited

U.S. PATENT DOCUMENTS

| | | | |
|---|---|---|---|
| 5,397,351 A | 3/1995 | Pavcnik et al. | |
| 5,411,552 A | 5/1995 | Andersen et al. | |
| 5,415,664 A * | 5/1995 | Pinchuk | 623/1.11 |
| 5,429,144 A * | 7/1995 | Wilk | 128/898 |
| 5,545,209 A | 8/1996 | Roberts et al. | |
| 5,554,185 A | 9/1996 | Block et al. | |
| 5,591,195 A | 1/1997 | Taheri et al. | |
| 5,618,300 A | 4/1997 | Marin et al. | |
| 5,702,368 A | 12/1997 | Stevens et al. | |
| 5,749,890 A | 5/1998 | Shaknovich | |
| 5,772,669 A * | 6/1998 | Vrba | 623/1.11 |
| 5,782,809 A | 7/1998 | Umeno et al. | |
| 5,855,597 A | 1/1999 | Jayaraman | |
| 5,855,601 A | 1/1999 | Bessler et al. | |
| 5,911,710 A | 6/1999 | Barry et al. | |
| 5,925,063 A | 7/1999 | Khosravi | |
| 5,957,949 A | 9/1999 | Leonhardt et al. | |
| 5,968,068 A | 10/1999 | Dehdashtian et al. | |
| 6,139,572 A * | 10/2000 | Campbell et al. | 623/1.11 |
| 6,162,208 A | 12/2000 | Hipps | |
| 6,168,614 B1 | 1/2001 | Andersen et al. | |
| 6,245,102 B1 | 6/2001 | Jayaraman | |
| 6,299,637 B1 | 10/2001 | Shaolia et al. | |
| 6,302,906 B1 | 10/2001 | Goicoechea et al. | |
| 6,425,916 B1 | 7/2002 | Garrison et al. | |
| 6,454,799 B1 | 9/2002 | Schreck | |
| 6,458,153 B1 | 10/2002 | Bailey et al. | |
| 6,569,196 B1 | 5/2003 | Vesely | |
| 6,605,112 B1 | 8/2003 | Moll et al. | |
| 6,697,667 B1 * | 2/2004 | Lee et al. | 600/479 |
| 6,730,118 B2 | 5/2004 | Spenser et al. | |
| 6,769,434 B2 | 8/2004 | Liddicoat | |
| 6,786,925 B1 | 9/2004 | Schoon | |
| 6,790,229 B1 | 9/2004 | Berreklouw | |
| 6,797,002 B2 | 9/2004 | Spence | |
| 6,821,297 B2 | 11/2004 | Snyders | |
| 6,830,584 B1 | 12/2004 | Seguin | |
| 6,830,585 B1 | 12/2004 | Artof | |
| 6,866,650 B2 | 3/2005 | Stevens | |
| 6,872,223 B2 | 3/2005 | Roberts | |
| 6,893,460 B2 | 5/2005 | Spenser et al. | |
| 6,908,481 B2 | 6/2005 | Cribier | |
| 6,951,571 B1 | 10/2005 | Srivastava | |
| 6,989,028 B2 | 1/2006 | Lashinski et al. | |
| 7,780,723 B2 | 8/2010 | Taylor | |
| 7,780,725 B2 | 8/2010 | Haug et al. | |
| 2001/0002445 A1 | 5/2001 | Vesely | |
| 2001/0007956 A1 | 7/2001 | Letac et al. | |
| 2001/0021825 A1 | 9/2001 | Becker et al. | |
| 2002/0029014 A1 | 3/2002 | Jayaraman | |
| 2002/0032481 A1 | 3/2002 | Gabbay | |
| 2002/0138138 A1 | 9/2002 | Yang | |
| 2003/0050694 A1 | 3/2003 | Yang et al. | |
| 2003/0069492 A1 | 4/2003 | Abrams et al. | |
| 2003/0109924 A1 | 6/2003 | Cribier | |
| 2003/0199963 A1 | 10/2003 | Tower et al. | |
| 2004/0039436 A1 | 2/2004 | Spenser et al. | |
| 2004/0068248 A1 | 4/2004 | Mooney et al. | |
| 2004/0093060 A1 | 5/2004 | Sequin et al. | |
| 2004/0097788 A1 | 5/2004 | Mourles et al. | |
| 2004/0111096 A1 | 6/2004 | Tu | |
| 2004/0122516 A1 | 6/2004 | Fogarty | |
| 2004/0167573 A1 | 8/2004 | Williamson | |
| 2004/0167620 A1 | 8/2004 | Ortiz | |
| 2004/0186563 A1 | 9/2004 | Lobbi | |
| 2004/0193261 A1 | 9/2004 | Berreklouw | |
| 2004/0210304 A1 | 10/2004 | Seguin et al. | |
| 2004/0210307 A1 | 10/2004 | Khairkhahan | |
| 2004/0215333 A1 | 10/2004 | Duran | |
| 2004/0225353 A1 | 11/2004 | McGuckin, Jr. | |
| 2004/0225354 A1 | 11/2004 | Allen | |
| 2004/0260394 A1 | 12/2004 | Douk et al. | |
| 2005/0010287 A1 | 1/2005 | Macoviak | |
| 2005/0033398 A1 | 2/2005 | Seguin | |
| 2005/0043790 A1 | 2/2005 | Seguin | |
| 2005/0049692 A1 | 3/2005 | Numamoto | |
| 2005/0049696 A1 | 3/2005 | Siess | |
| 2005/0060029 A1 | 3/2005 | Le | |
| 2005/0075584 A1 | 4/2005 | Cali | |
| 2005/0075712 A1 | 4/2005 | Biancucci | |
| 2005/0075717 A1 | 4/2005 | Nguyen | |
| 2005/0075719 A1 | 4/2005 | Bergheim | |
| 2005/0075724 A1 | 4/2005 | Svanidze | |
| 2005/0075730 A1 | 4/2005 | Myers | |
| 2005/0075731 A1 | 4/2005 | Artof | |
| 2005/0096738 A1 | 5/2005 | Cali | |
| 2005/0113910 A1 | 5/2005 | Paniagua | |
| 2005/0131438 A1 | 6/2005 | Cohn | |
| 2005/0137686 A1 | 6/2005 | Salahieh | |
| 2005/0137692 A1 | 6/2005 | Haug | |
| 2005/0137695 A1 | 6/2005 | Salahieh | |
| 2005/0137701 A1 | 6/2005 | Salahieh | |
| 2005/0143809 A1 | 6/2005 | Salahieh | |
| 2005/0203549 A1 | 9/2005 | Realyvasquez | |
| 2005/0203618 A1 | 9/2005 | Sharkawy | |
| 2005/0228495 A1 | 10/2005 | Macoviak | |
| 2005/0234546 A1 | 10/2005 | Nugent | |
| 2005/0240200 A1 | 10/2005 | Bergheim | |
| 2006/0004439 A1 | 1/2006 | Spenser et al. | |
| 2006/0155366 A1 | 7/2006 | LaDuca et al. | |
| 2007/0088431 A1 | 4/2007 | Bourang | |
| 2008/0125861 A1 * | 5/2008 | Webler et al. | 623/2.36 |

FOREIGN PATENT DOCUMENTS

| | | |
|---|---|---|
| WO | WO 02/060352 | 8/2002 |
| WO | WO 03/030776 | 4/2003 |
| WO | WO 2004/019825 | 11/2004 |
| WO | WO2005/104957 | 11/2005 |
| WO | WO2006/091597 | 8/2006 |

OTHER PUBLICATIONS

PCT International Search Report for Application No. PCT/US2007/078053, dated Jul. 17, 2008.

* cited by examiner

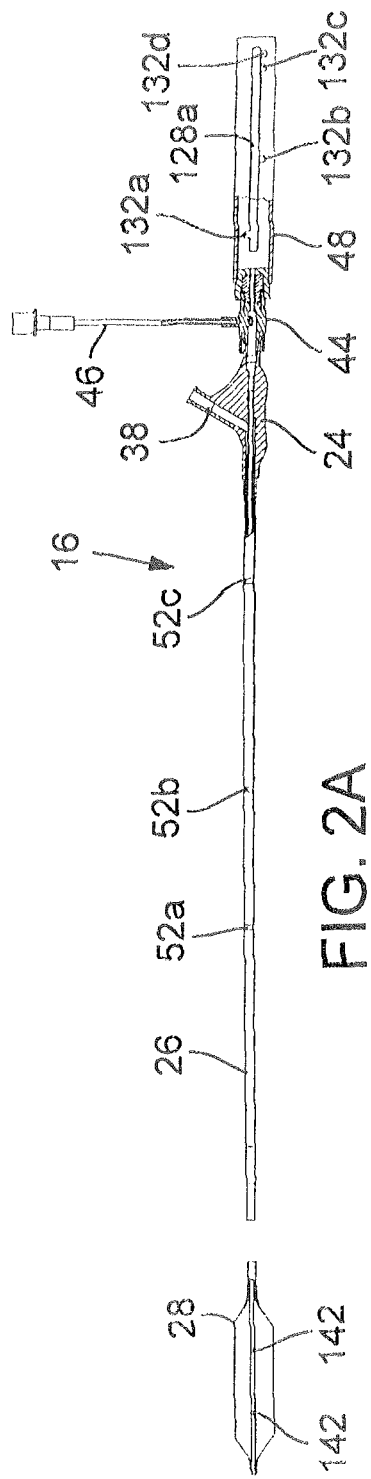
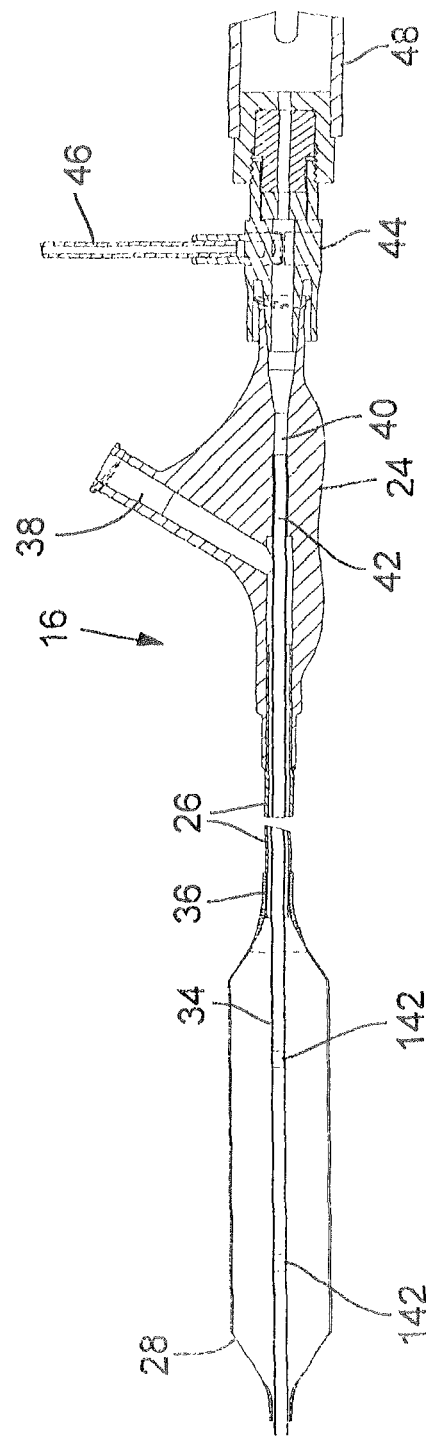
FIG. 2A
FIG. 2B

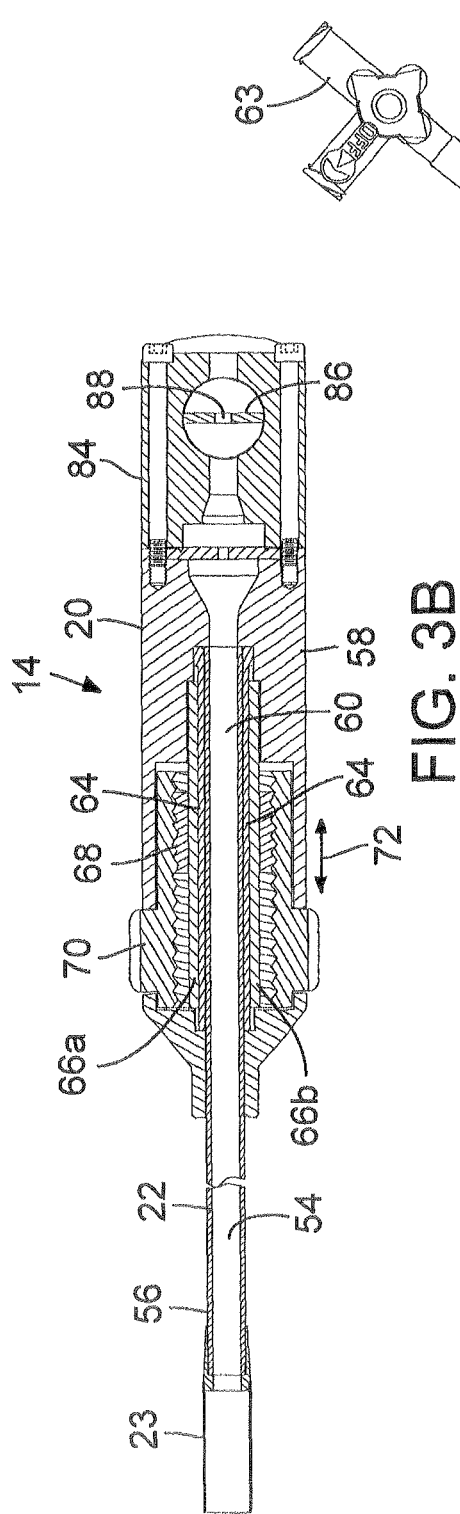
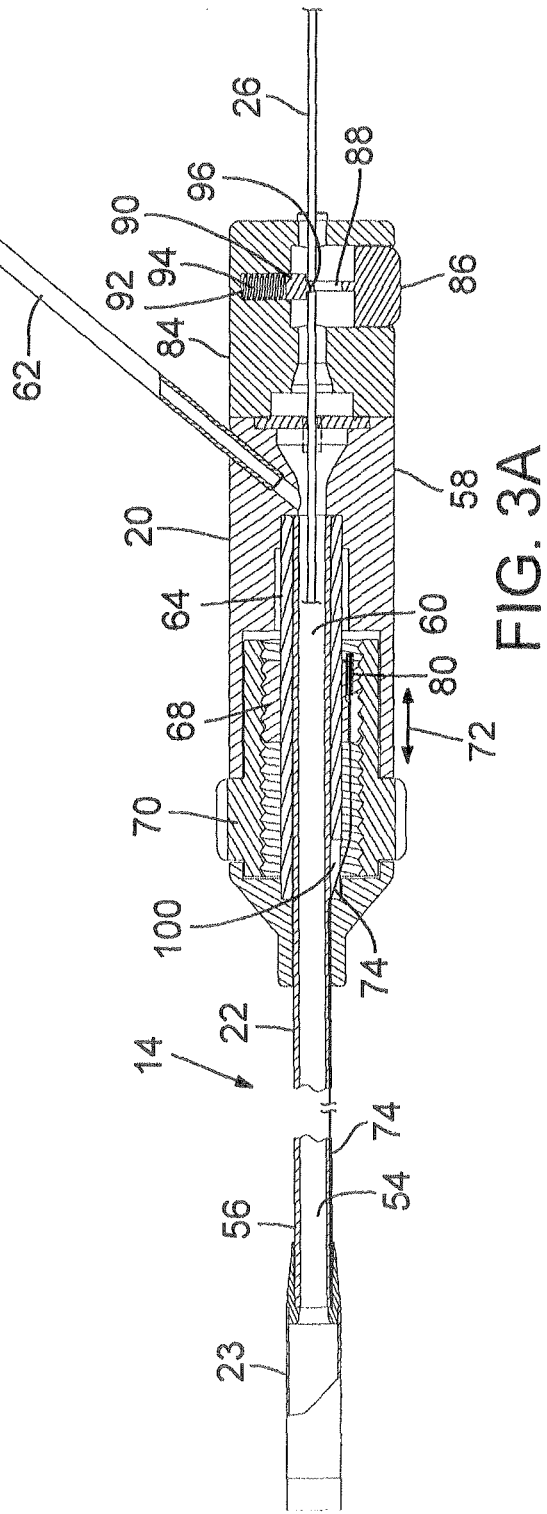

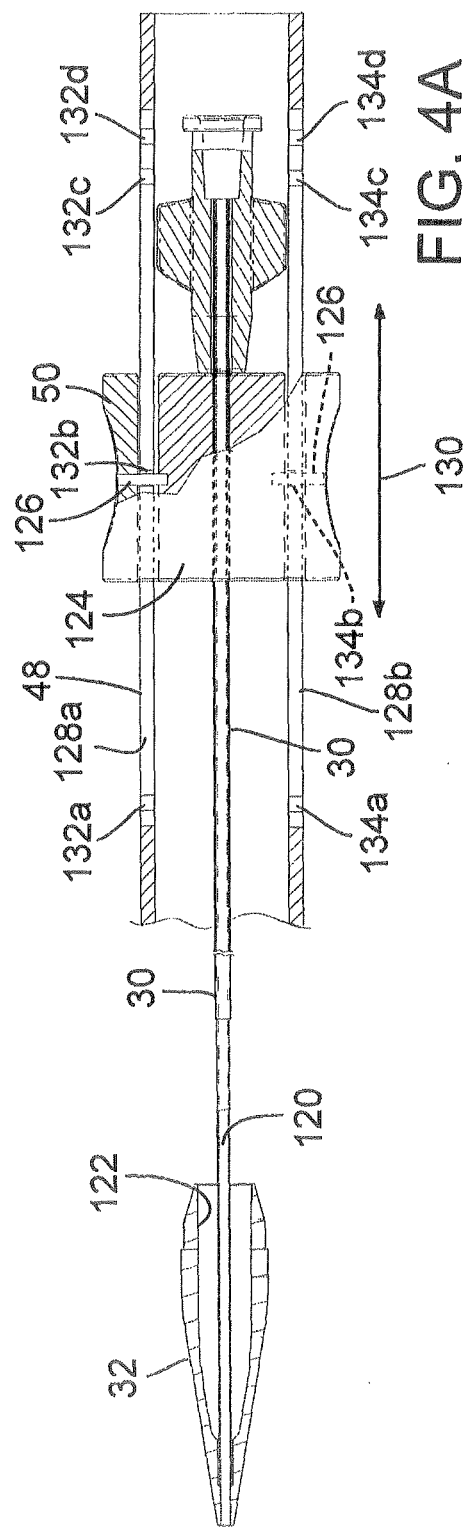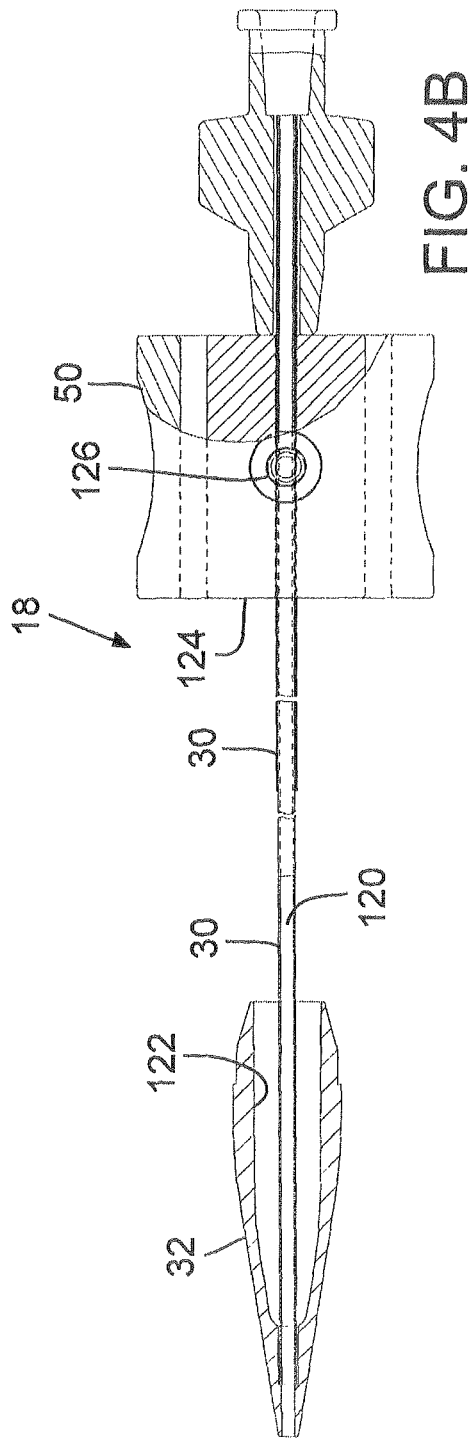

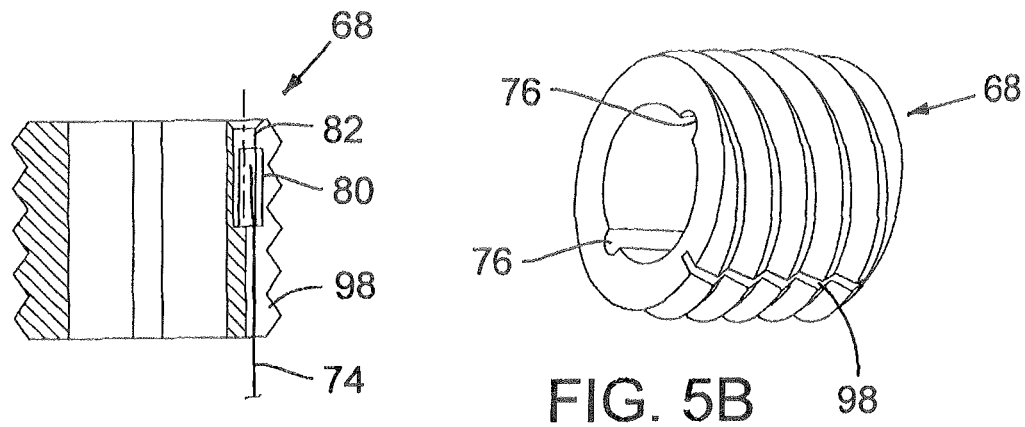
FIG. 5A
FIG. 5B
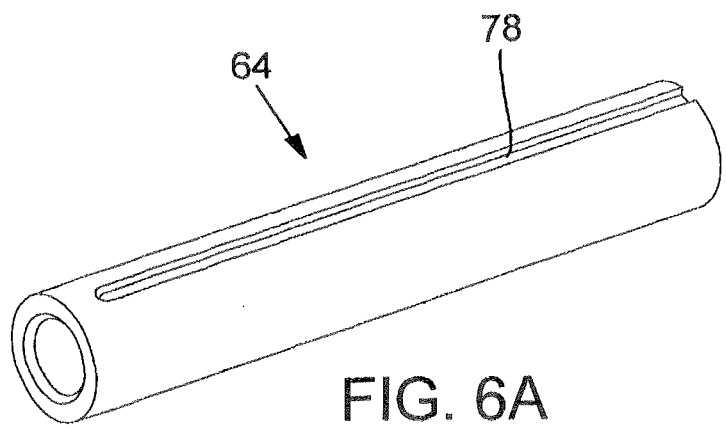
FIG. 6A
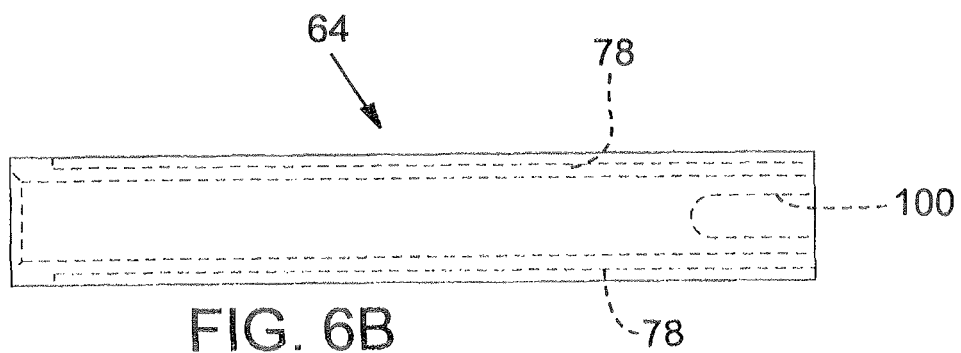
FIG. 6B

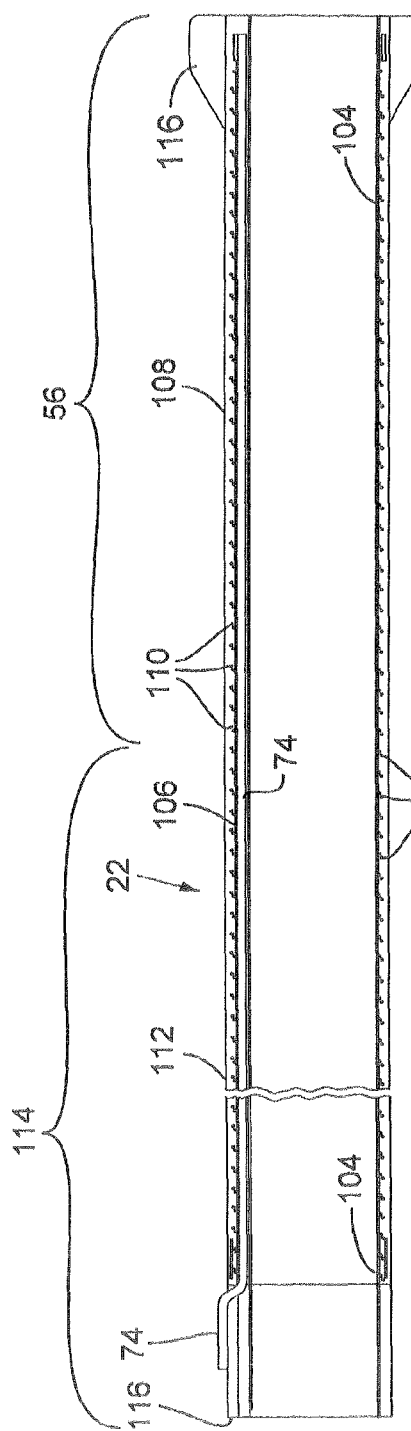
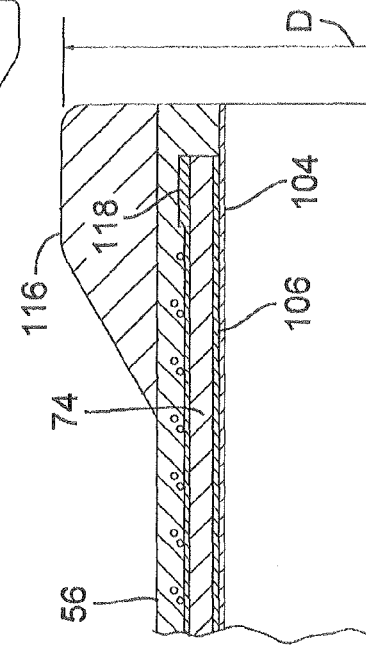
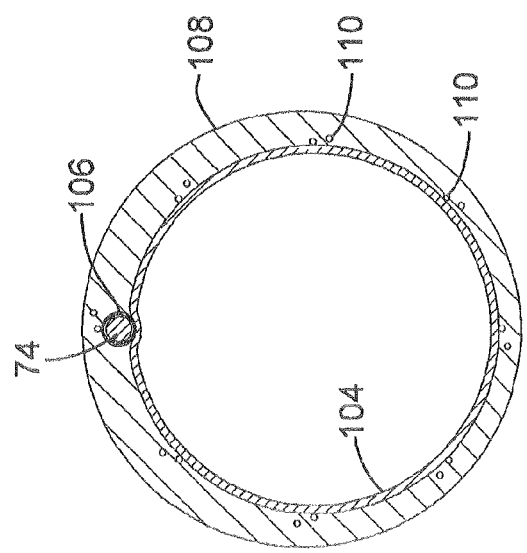

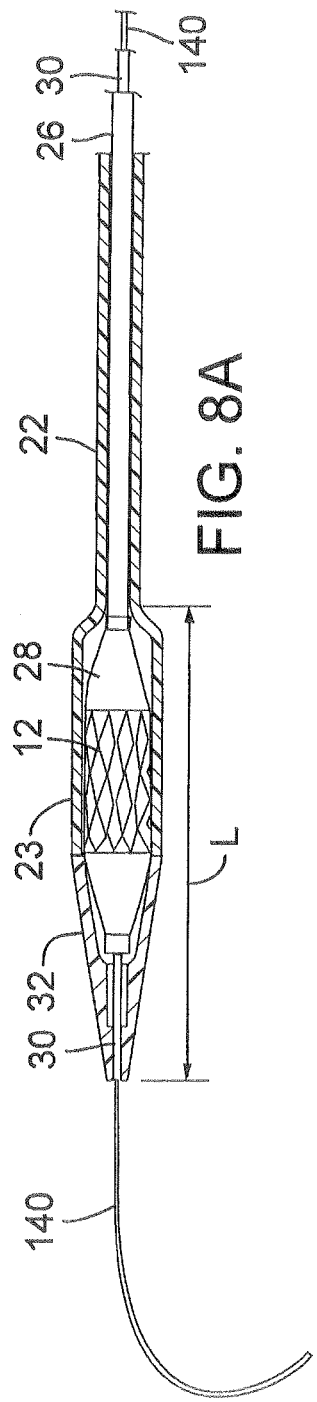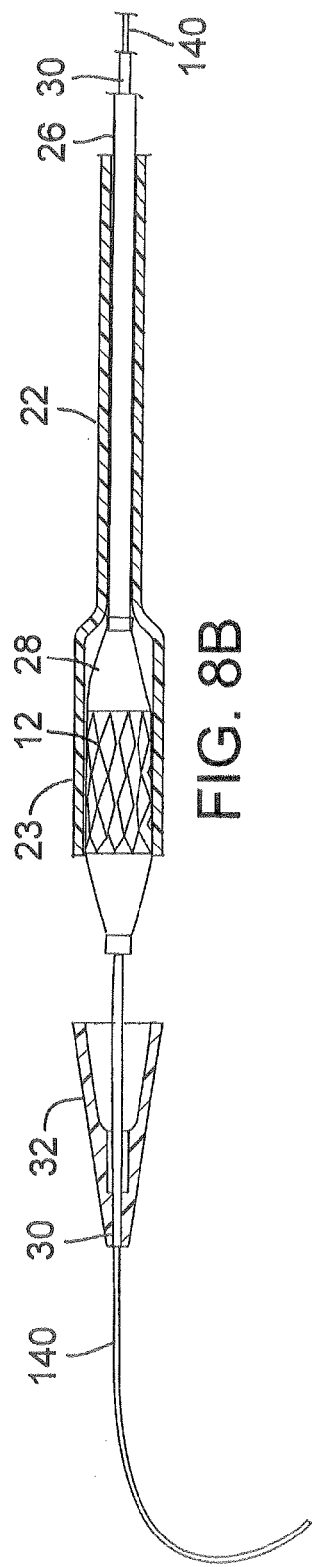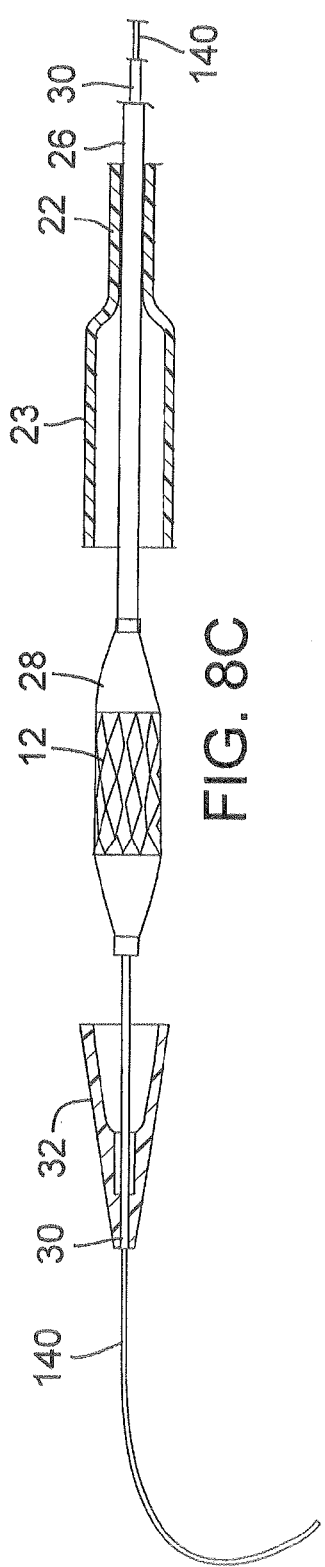

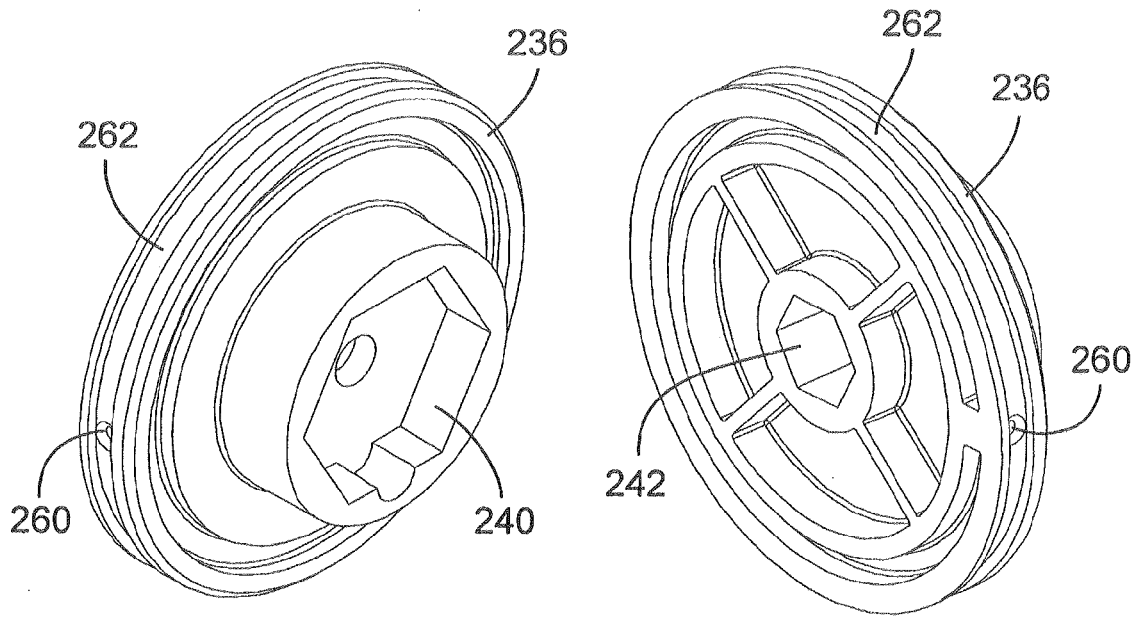
FIG. 16A
FIG. 16B
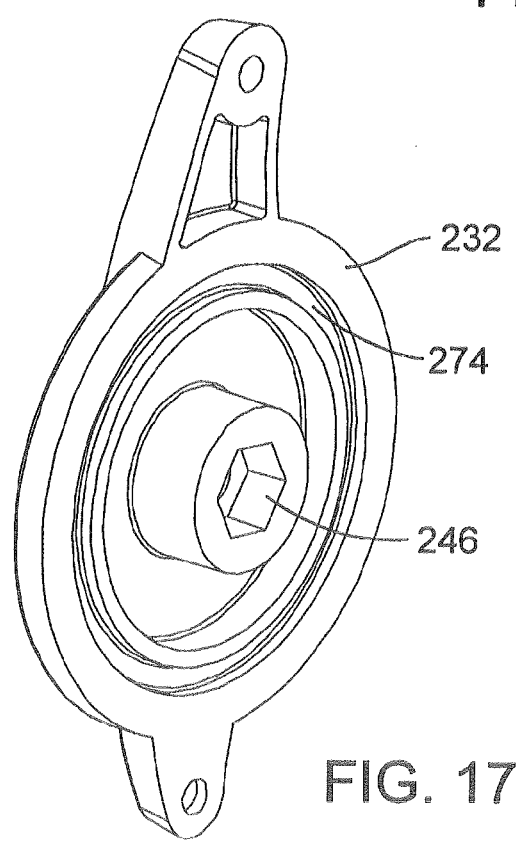
FIG. 17

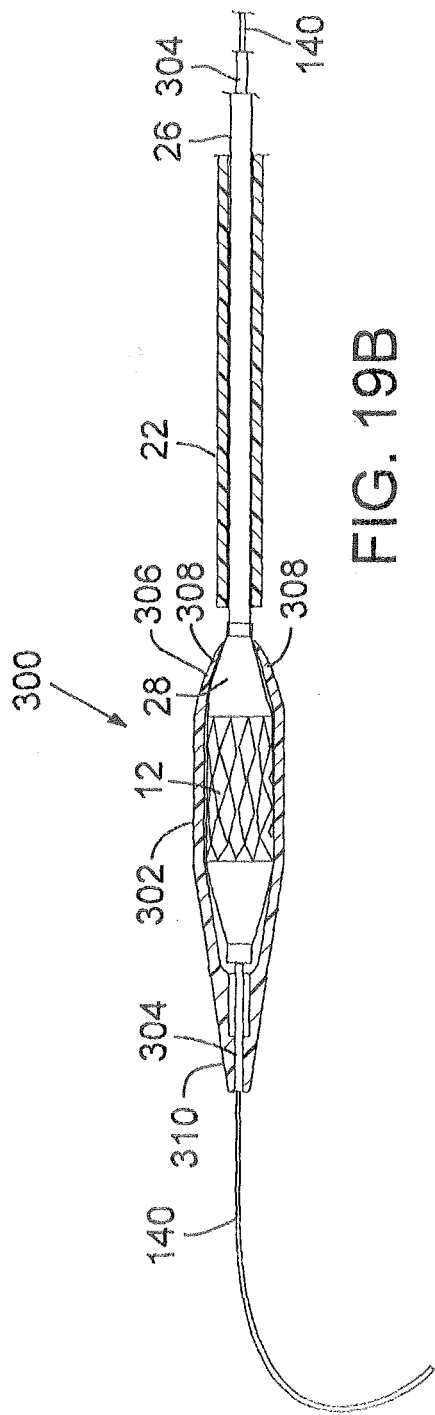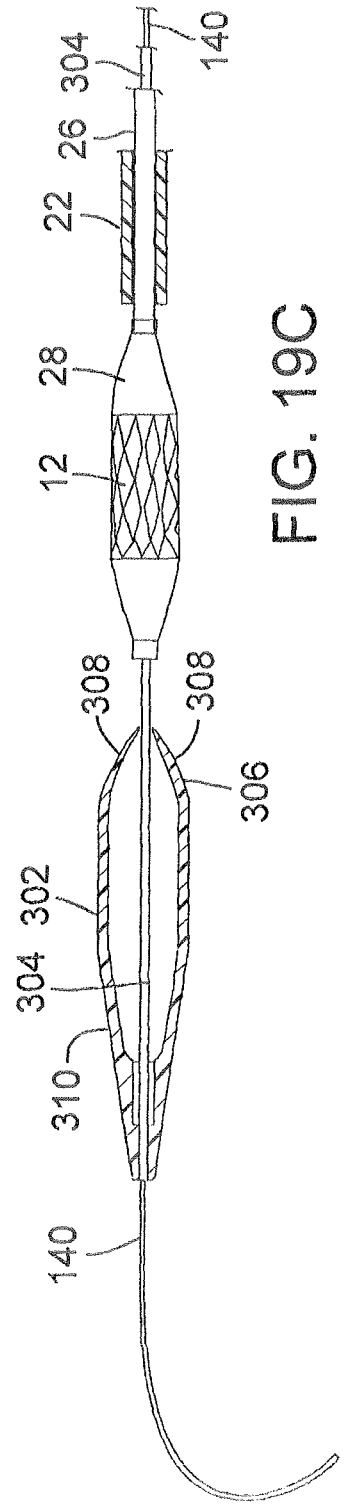

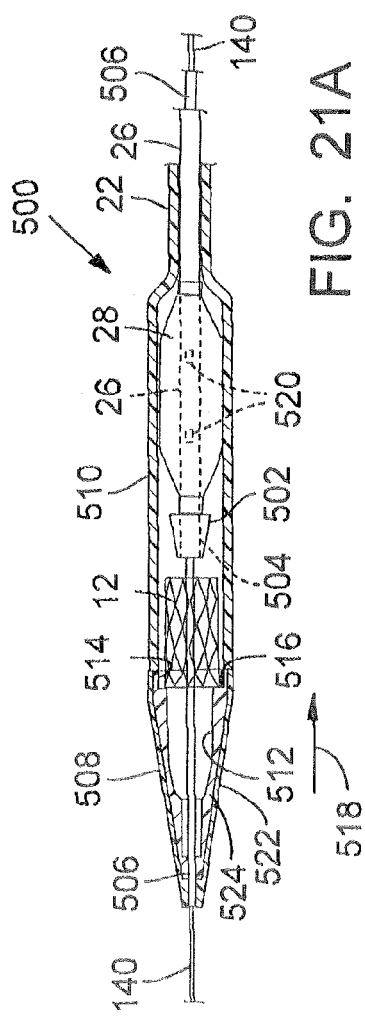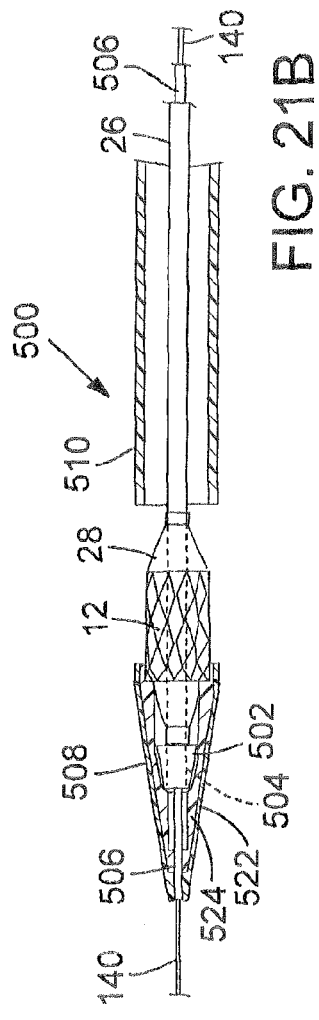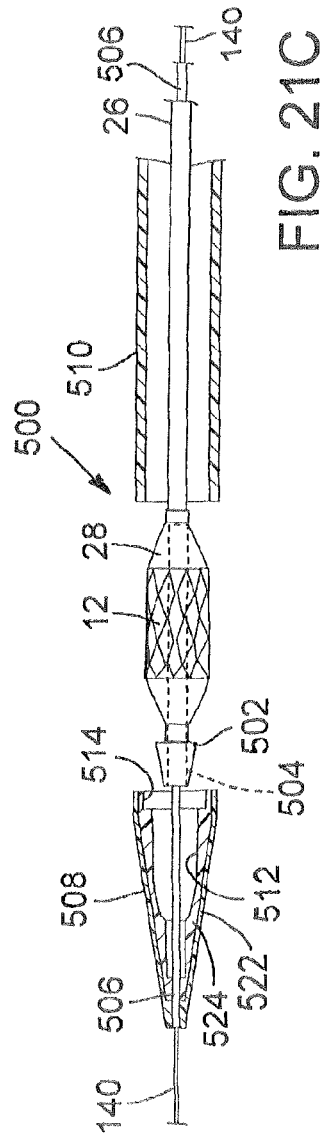

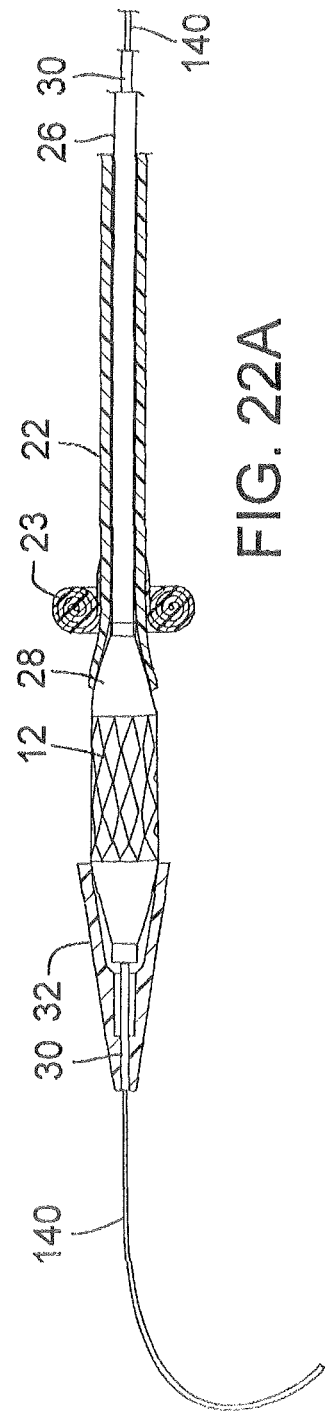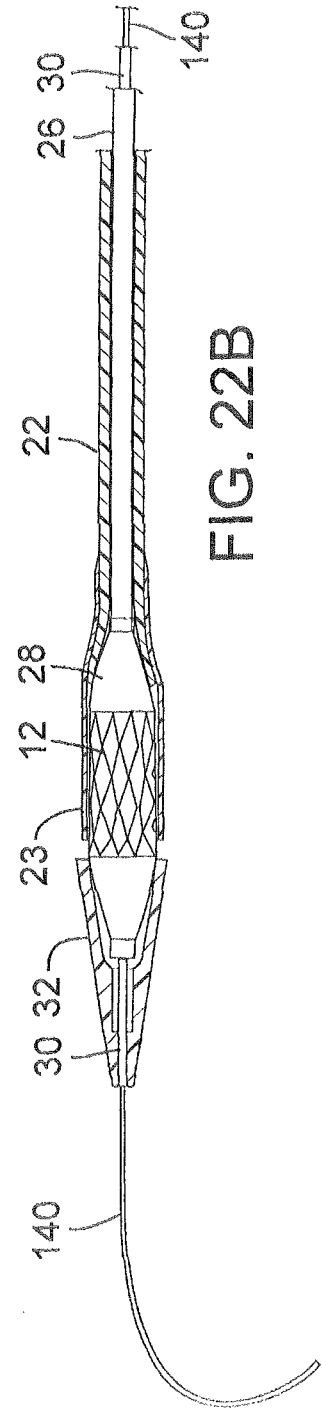

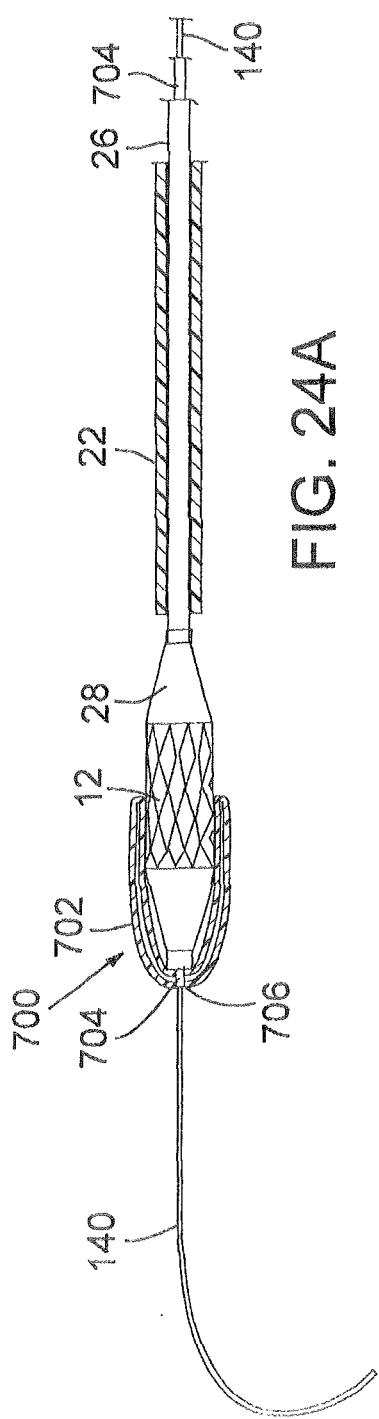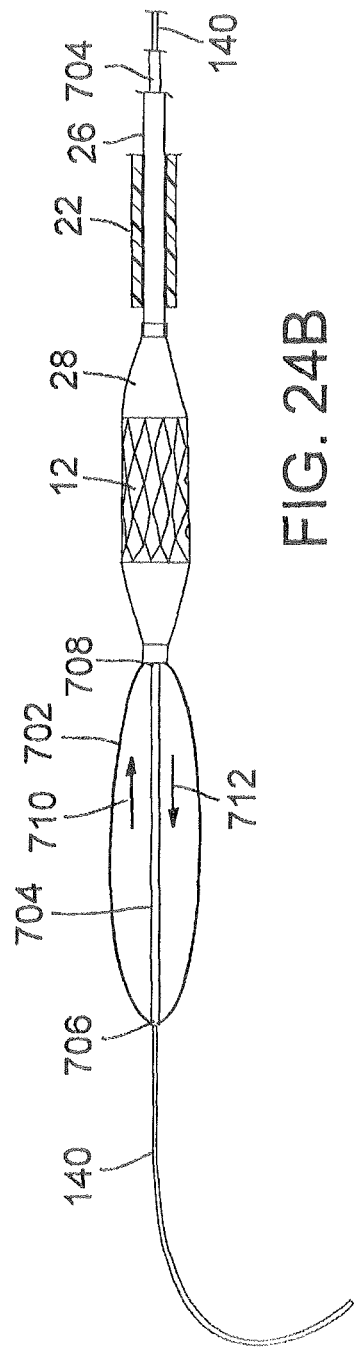

INTEGRATED HEART VALVE DELIVERY SYSTEM

CROSS REFERENCE TO RELATED APPLICATION

The present application claims the benefit of U.S. Provisional Application No. 60/843,470, filed Sep. 8, 2006, which is incorporated herein by reference.

FIELD

The present application concerns embodiments of a system for delivering a prosthetic valve to a heart via the patient's vasculature.

BACKGROUND

Endovascular delivery catheters are used to implant prosthetic devices, such as a prosthetic valve, at locations inside the body that are not readily accessible by surgery or where access without surgery is desirable. The usefulness of delivery catheters is largely limited by the ability of the catheter to successfully navigate through small vessels and around tight bends in the vasculature, such as around the aortic arch.

Known delivery apparatuses include a balloon catheter having an inflatable balloon that mounts a prosthetic valve in a crimped state and a retractable cover that extends over the valve to protect the interior walls of the vasculature as the valve is advanced to the implantation site. Various techniques have been employed to adjust the curvature of a section of the delivery apparatus to help "steer" the valve through bends in the vasculature. The balloon catheter may also include a tapered tip portion mounted distal to the balloon to facilitate tracking through the vasculature. The tip portion, however, increases the length of the relatively stiff, non-steerable section of the apparatus. Unfortunately, due to the relatively long stiff section, successful delivery of a prosthetic valve through tortuous vasculature, such as required for retrograde delivery of a prosthetic aortic heart valve, has proven to be difficult.

A known technique for adjusting the curvature of a delivery apparatus employs a pull wire having a distal end fixedly secured to the steerable section and a proximal end operatively connected to a rotatable adjustment knob located outside the body. Rotation of the adjustment applies a pulling force on the pull wire, which in turn causes the steerable section to bend. The rotation of the adjustment knob produces less than 1:1 movement of the pull wire; that is, rotation of the knob does not produce equal movement of the steerable section. To facilitate steering, it would be desirable to provide an adjustment mechanism that can produce substantially 1:1 movement of the steerable section.

It is also known to use an introducer sheath for safely introducing a delivery apparatus into the patient's vasculature (e.g., the femoral artery). An introducer sheath has an elongated sleeve that is inserted into the vasculature and a seal housing that contains one or more sealing valves that allow a delivery apparatus to be placed in fluid communication with the vasculature with minimal blood loss. A conventional introducer sheath typically requires a tubular loader to be inserted through the seals in the sheath housing to provide an unobstructed path through the seal housing for a valve mounted on a balloon catheter. A conventional loader extends from the proximal end of the introducer sheath, and therefore decreases the available working length of the delivery apparatus that can be inserted through the sheath and into the body.

Accordingly, there remains a need in the art for improved endovascular systems for implanting valves and other prosthetic devices.

SUMMARY

Certain embodiments of the present disclosure provide a heart valve delivery apparatus for delivery of a prosthetic heart valve to a native valve site via the human vasculature. The delivery apparatus is particularly suited for advancing a prosthetic valve through the aorta (i.e., in a retrograde approach) for replacing a stenotic native aortic valve.

The delivery apparatus in particular embodiments includes a balloon catheter having an inflatable balloon which mounts a crimped valve for delivery through the patient's vasculature. The delivery apparatus can include a guide, or flex, catheter having a shaft that extends over the shaft of the balloon catheter. The guide catheter shaft has a steerable section, the curvature of which can be adjusted by the operator to facilitate navigation of the delivery apparatus around bends in the vasculature. The delivery apparatus also can include a nose catheter having a shaft that extends through the balloon catheter shaft and a nose piece located distally of the valve. The nose piece desirably has a tapered outer surface and is made of a flexible material to provide atraumatic tracking through the arteries and a stenotic native valve. The nose piece desirably has an internal bore that is dimensioned to receive at least a distal end portion of the deflated balloon during delivery of the valve.

By inserting a portion of the balloon into the nose piece, the length of the non-steerable section of the delivery apparatus can be reduced (e.g., by about 1.5 to 2.0 cm in some examples), which greatly enhances the ability of the delivery apparatus to track through the aortic arch with little or no contact between the end of the delivery apparatus and the inner walls of the aorta. Once the delivery apparatus has been advanced to the implantation site, the nose catheter can be moved distally relative to the balloon catheter to withdraw the balloon from the nose piece so as not to interfere with inflating the balloon.

The guide catheter shaft can be provided with a cover at its distal end to cover a portion of the balloon and/or the valve that is not already covered by the nose piece. In particular embodiments, the cover extends over the remaining portion of the balloon and the valve that is not covered by the nose piece. In this manner, the entire outer surface of the valve and the balloon are shielded by the nose piece and the cover. Consequently, an introducer sheath need not be used to introduce the delivery apparatus into the patient's vasculature. Unlike an introducer sheath, the cover need only be in contact with the femoral and iliac arteries for only a short period of time, and thus minimizes the possibility of trauma to these vessels. Further, by eliminating the introducer sheath, the maximum diameter of the system can be reduced, and therefore it is less occlusive to the femoral artery.

In one variation of the delivery apparatus, the nose piece has an internal bore dimensioned to receive the entire valve and substantially the entire balloon during delivery of the valve. Thus, in this embodiment, the cover attached to the end of the guide catheter need not be provided. In another variation, the cover of the guide catheter extends completely over the valve and the balloon, and the nose catheter is not provided. The cover can be an expandable mesh basket that can collapse around the valve and the balloon to provide a smooth tracking profile. The mesh basket can be expanded by the operator, such as by pulling one or more pull wires, which dilates a distal opening in the mesh basket permitting the balloon and the valve to be advanced from the basket for deployment.

As noted above, the guide catheter desirably has a steerable section that can be deflected or bent by the operator to assist in tracking the delivery apparatus around bends in the vasculature. In certain embodiments, the guide catheter can be provided with a manually operated adjustment mechanism that produces substantially 1:1 movement of the steerable section. To such ends, the adjustment mechanism can include a pivotable lever that is operatively coupled to the steerable section via a pull wire extending through a lumen in the guide catheter shaft. Pivoting the lever operates a pulley, which retracts the pull wire, producing substantially 1:1 movement of the steerable section. Pivoting the lever in the opposite direction releases tension in the pull wire, and the resiliency of the steerable section causes the steerable section to return to its normal, non-deflected shape.

In cases where an introducer sheath is used to assist in inserting the delivery apparatus into the patient's vasculature, the introducer sheath can be provided with an integrated loader tube that extends into the seal housing of the sheath. The loader tube is connected to an end piece coupled to the distal end of the seal housing. The end piece is moveable along the length of the seal housing between a first, extended position where the loader tube is spaced from the sealing valves in the seal housing and a second, retracted position where the loader tube extends through the sealing valves to provide an unobstructed pathway for a valve mounted on a balloon catheter. Because the loader tube does not extend behind the end piece, the loader tube does not decrease the available working length of the delivery apparatus that can be inserted through the sheath and into the vasculature.

In one representative embodiment, an apparatus for delivering a prosthetic valve through the vasculature of a patient comprises a balloon catheter, a guide catheter, and a nose catheter configured to move longitudinally relative to each other. The balloon catheter comprises an elongated shaft and a balloon connected to a distal end portion of the shaft, the balloon being adapted to carry the valve in a crimped state and being inflatable to deploy the valve at an implantation site in the patient's body. The guide catheter comprises an elongated shaft extending over the balloon catheter shaft, the shaft of the guide catheter comprising a steerable section. The guide catheter further comprises an adjustment mechanism operatively coupled to the steerable section. The adjustment mechanism is configured to adjust the curvature of the steerable section and the portion of the balloon catheter shaft extending through the steerable section. The nose catheter comprises an elongated shaft extending through the balloon catheter shaft and a nose piece connected to a distal end of the nose catheter shaft. The nose piece has an internal bore adapted to receive at least a distal end portion of the balloon in a deflated state during delivery of the valve.

In another representative embodiment, a method of implanting a prosthetic valve at an implantation site in a patient's body comprises placing the valve on an inflatable balloon of a balloon catheter of a delivery apparatus and inserting at least a distal end portion of the balloon in a nose piece of a nose catheter of the delivery apparatus. The balloon catheter and the nose catheter are then inserted into the body and advanced through the patient's vasculature. At or near the implantation site, the nose catheter is moved distally relative to the balloon catheter to uncover the portion of the balloon inside the nose piece, and thereafter the valve can be deployed at the implantation site by inflating the balloon.

In another representative embodiment, a method of implanting a prosthetic valve at an implantation site in a patient's body comprises placing the valve in a crimped state on the distal end portion of an elongated delivery apparatus and advancing the delivery apparatus through the patient's vasculature. Subsequent to the act of advancing the delivery apparatus, the crimped valve is moved onto an inflatable balloon on the distal end portion of the delivery apparatus and then deployed at the implantation site by inflating the balloon.

In yet another representative embodiment, an apparatus for delivering a prosthetic valve through the vasculature of a patient comprises a balloon catheter and a nose catheter. The balloon catheter comprises an elongated shaft, a balloon connected to a distal end portion of the shaft, and a tapered wedge connected to the distal end portion adjacent the balloon. The nose catheter comprises an elongated shaft extending through the shaft of the balloon catheter, the balloon, and the wedge. The nose catheter further includes a nose piece connected to a distal end of the nose catheter shaft. The valve can be mounted in a crimped state between the nose piece and the wedge. The nose piece can be retracted proximally to push the valve over the wedge and onto the balloon, with the wedge partially expanding the valve before it is placed on the balloon.

In another representative embodiment, a guide catheter for an endovascular delivery apparatus comprises an elongated shaft having a steerable section, a handle comprising a pivotable lever, and a pull wire. The pull wire has a proximal end portion coupled to the lever and a distal end portion fixedly secured to the steerable section such that pivoting movement of the lever applies a pulling force on the pull wire to cause the steerable section to bend.

In another representative embodiment, an endovascular delivery apparatus comprises a balloon catheter comprising an elongated shaft and a balloon connected to a distal end portion of the shaft. A guide catheter comprises an elongated shaft comprising an inner polymeric tubular liner having a lumen sized to permit insertion of the balloon and the balloon catheter shaft therethrough. The shaft further comprises a braided metal layer surrounding the tubular liner, and an outer polymeric layer surrounding the braided metal layer.

In another representative embodiment, a method for making a catheter comprises forming an inner tubular layer from a polymeric material, the inner tubular layer having a lumen dimensioned to allow a balloon of a balloon catheter to pass therethrough, forming a tubular pull wire conduit from a polymeric material, placing the conduit and the inner tubular layer side-by-side in a parallel relationship relative to each other, forming a braided metal layer around the conduit and the inner tubular layer, and forming an outer polymeric layer around the braided metal layer.

In another representative embodiment, an introducer sheath comprises an elongated tubular sleeve having a lumen and adapted to be inserted into a patient's vasculature, a seal housing comprising an inner bore in communication with the lumen of the sleeve and one or more sealing valves housed in the bore, and an end piece coupled to the sealing housing opposite the sleeve. The end piece comprises a loader tube extending into the bore and is moveable along a length of the seal housing to move the loader tube from a first position spaced from the one or more sealing valves to a second position wherein the loader tube extends through the sealing valves.

The foregoing and other features and advantages of the invention will become more apparent from the following detailed description, which proceeds with reference to the accompanying figures.

BRIEF DESCRIPTION OF THE DRAWINGS

FIG. 2A is side view of the balloon catheter of the delivery apparatus of FIG. 1, shown partially in section.

FIG. 2B is an enlarged, cross-sectional view of the balloon catheter shown in FIG. 2A, taken along the length of the catheter.

FIG. 3A is a cross-sectional view of the guide catheter of the delivery apparatus of FIG. 1, taken along a plane extending along the length of the guide catheter.

FIG. 3B is a cross-sectional view of the guide catheter, taken along a plane that is perpendicular to the plane defining the cross-section view shown in FIG. 3A.

FIG. 4A is a cross-sectional view of the nose catheter of the delivery apparatus shown in FIG. 1, taken along the length of the nose catheter.

FIG. 4B is an enlarged, cross-sectional view of the nose catheter.

FIGS. 5A and 5B are cross-sectional and perspective views, respectively, of a slide nut used in the handle portion of the guide catheter.

FIGS. 6A and 6B are perspective and side views, respectively, of an inner sleeve used in the handle portion of the guide catheter.

FIG. 7A is a cross-sectional view of a guide catheter, according to one embodiment, taken along the length thereof.

FIG. 7B is a transverse cross-sectional view of the guide catheter shown in FIG. 7A.

FIG. 7C is an enlarged, longitudinal cross-sectional view of the distal end portion of the guide catheter shown in FIG. 7A.

FIGS. 8A-8C are cross-sectional views of the distal end portion of the delivery apparatus of FIG. 1, illustrating the operation of the same for implanting a prosthetic valve.

FIGS. 16A and 16B are perspective views of a pulley used in the guide catheter of FIG. 11.

FIG. 17 is a perspective view of a lever portion used in the guide catheter of FIG. 11.

FIGS. 19B and 19C are cross-sectional views illustrating the operation of the nose catheter shown in FIG. 19A.

FIGS. 21A-21C are cross-sectional views of an alternative embodiment of a delivery apparatus, illustrating the operation of the same for implanting a prosthetic valve.

FIGS. 22A and 22B are cross-sectional views of the distal end portion of another embodiment of a delivery apparatus.

FIGS. 24A-24B are cross-sectional views of another embodiment of a delivery apparatus.

DETAILED DESCRIPTION

Figure 1:
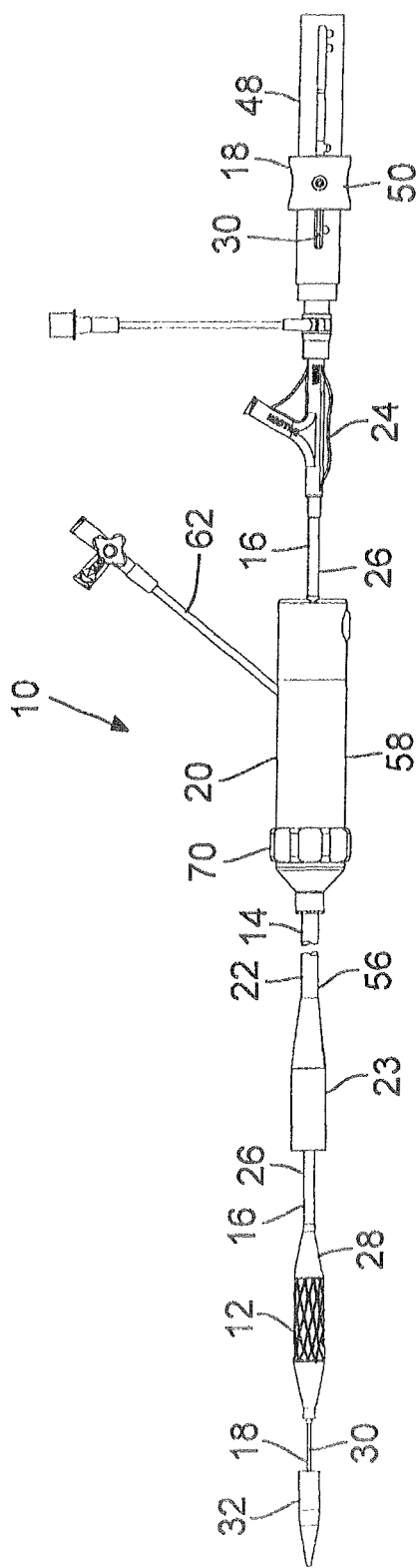
FIG. 1 is side view of an endovascular delivery apparatus for implanting a prosthetic valve, according to one embodiment.

FIG. 1 shows a delivery apparatus 10 adapted to deliver a prosthetic heart valve 12 (e.g., a prosthetic aortic valve) to a heart, according to one embodiment. The apparatus 10 generally includes a steerable guide catheter 14 (also referred to as a flex catheter), a balloon catheter 16 extending through the guide catheter 14, and a nose catheter 18 extending through the balloon catheter 16. The guide catheter 14, the balloon catheter 16, and the nose catheter 18 in the illustrated embodiment are adapted to slide longitudinally relative to each other to facilitate delivery and positioning of the valve 12 at an implantation site in a patient's body, as described in detail below.

The guide catheter 14 includes a handle portion 20 and an elongated guide tube, or shaft, 22 extending from the handle portion 20. The balloon catheter 16 includes a proximal portion 24 adjacent the handle portion 20 and an elongated shaft 26 that extends from the proximal portion 24 and through the handle portion 20 and the guide tube 22. An inflatable balloon 28 is mounted at the distal end of the balloon catheter. The valve 12 is shown mounted on the balloon 28 in a crimped state having a reduced diameter for delivery to the heart via the patient's vasculature.

The nose catheter 18 includes an elongated shaft 30 that extends through the proximal portion 24, the shaft 26, and the balloon 28 of the balloon catheter. The nose catheter 18 further includes a nose piece 32 mounted at the distal end of the shaft 30 and adapted to receive a distal end portion of the balloon when the apparatus 10 is used to advance the valve through the patient's vasculature to the implantation site.

As can be seen in FIGS. 2A and 2B, the balloon catheter 16 in the illustrated configuration further includes an inner shaft 34 (FIG. 2B) that extends from the proximal portion 24 and coaxially through the outer shaft 26 and the balloon 28. The balloon 28 can be supported on a distal end portion of the inner shaft 34 that extends outwardly from the outer shaft 26 with a proximal end portion 36 of the balloon secured to the distal end of the outer shaft 26 (e.g., with a suitable adhesive). The outer diameter of the inner shaft 34 is sized such that an annular space is defined between the inner and outer shafts along the entire length of the outer shaft. The proximal portion 24 of the balloon catheter can be formed with a fluid passageway 38 that is fluidly connectable to a fluid source (e.g., a water source) for inflating the balloon. The fluid passageway 38 is in fluid communication with the annular space between the inner shaft 34 and the outer shaft 26 such that fluid from the fluid source can flow through the fluid passageway 38, through the space between the shafts, and into the balloon 28 to inflate the same and deploy the valve 12.

The proximal portion 24 also defines an inner lumen 40 that is in communication with a lumen 42 of the inner shaft 34. The lumens 40, 42 in the illustrated embodiment are sized to receive the shaft 30 of the nose catheter. The balloon catheter 16 also can include a coupler 44 connected to the proximal portion 24 and a tube 46 extending from the coupler. The tube 46 defines an internal passage which fluidly communicates with the lumen 40. The balloon catheter 16 also can include a slide support 48 connected to the proximal end of the coupler 44. The slide support 48 supports and cooperates with an adjustment ring 50 (FIGS. 1 and 4A-4B) of the nose catheter 18 to allow the nose catheter to be maintained at selected longitudinal positions relative to the balloon catheter 16, as described in greater detail below.

As shown in FIG. 2A, the outer surface of the outer shaft 26 can include one or more annular grooves or notches 52a, 52b, 52c spaced apart from each other along the proximal end portion of the shaft 26. The grooves cooperate with a locking mechanism 84 of the guide catheter 14 (FIGS. 3A-3B) to allow the guide catheter 14 to be maintained at selected longitudinal positions relative to the balloon catheter 16, as described in greater detail below.

The inner shaft 34 and the outer shaft 26 of the balloon catheter can be formed from any of various suitable materials, such as nylon, braided stainless steel wires, or a polyether block amide (commercially available as Pebax®). The shafts 26, 34 can have longitudinal sections formed from different materials in order to vary the flexibility of the shafts along their lengths. The inner shaft 34 can have an inner liner or layer formed of Teflon® to minimize sliding friction with the nose catheter shaft 30.

The guide catheter 14 is shown in greater detail in FIGS. 3A and 3B. As discussed above, the guide catheter 14 includes a handle portion 20 and an elongated guide tubes or shaft, 22 extending distally therefrom. The guide tube 22 defines a lumen 54 sized to receive the outer shaft 26 of the balloon catheter and allow the balloon catheter to slide longitudinally relative to the guide catheter. The distal end portion of the guide tube 22 comprises a steerable section 56, the curvature of which can be adjusted by the operator to assist in guiding the apparatus through the patient's vasculature, and in particular, the aortic arch.

The guide catheter desirably includes a cover, or shroud, 23 secured to the distal end of the guide tube 22. The cover 23 in particular embodiments is sized and shaped to receive the valve 12 crimped around the balloon and to abut against the proximal end surface of the nose piece 32, which is adapted to cover a distal end portion of the balloon 28 (as shown in FIG. 8A). Thus, when the apparatus is advanced to the deployment site, the valve 12 and the balloon 28 can be completely enclosed within the cover 23 and the nose piece 32.

As further shown in FIGS. 3A and 3B, the handle portion 20 includes a main body, or housing, 58 formed with a central lumen 60 that receives the proximal end portion of the guide tube 22. The handle portion 20 can include a side arm 62 defining an internal passage which fluidly communicates with the lumen 60. A stopcock 63 can be mounted on the upper end of the side arm 62.

The handle portion 20 is operatively connected to the steerable section 56 and functions as an adjustment to permit operator adjustment of the curvature of the steerable section 56 via manual adjustment of the handle portion. In the illustrated embodiment, for example, the handle portion 20 includes an inner sleeve 64 that surrounds a portion of the guide tube 22 inside the handle body 58. A threaded slide nut 68 is disposed on and slidable relative to the sleeve 64. The slide nut 68 is formed with external threads that mate with internal threads of an adjustment knob 70.

As best shown in FIGS. 5A and 5B, the slide nut 68 is formed with two slots 76 formed on the inner surface of the nut and extending the length thereof. As best shown in FIGS. 6A and 6B, the sleeve 64 is also formed with longitudinally extending slots 78 that are aligned with the slots 76 of the slide nut 68 when the slide nut is placed on the sleeve. Disposed in each slot 78 is a respective elongated nut guide 66a, 66b (FIG. 3B), which can be in the form of an elongated rod or pin. The nut guides 66a, 66b extend radially into respective slots 76 in the slide nut 68 to prevent rotation of the slide nut 68 relative to the sleeve 64. By virtue of this arrangement, rotation of the adjustment knob 70 (either clockwise or counterclockwise) causes the slide nut 68 to move longitudinally relative to the sleeve 64 in the directions indicated by double-headed arrow 72.

One or more pull wires 74 connect the adjustment knob 70 to the steerable section 56 to produce movement of the steerable section upon rotation of the adjustment knob. In certain embodiments, the proximal end portion of the pull wire 74 can extend into and can be secured to a retaining pin 80 (FIG. 3A), such as by crimping the pin 80 to the pull wire. The pin 80 is disposed in a slot 82 in the slide nut 68 (as best shown in FIG. 5A). The pull wire 74 extends from pin 80, through a slot 98 in the slide nut, a slot 100 in the sleeve 64, and into and through a pull wire lumen in the shaft 22 (FIG. 3A). The distal end portion of the pull wire 74 is secured to the distal end portion of the steerable section 56.

The pin 80, which retains the proximal end of the pull wire 74, is captured in the slot 82 in the slide nut 68. Hence, when the adjustment knob 70 is rotated to move the slide nut 68 in the proximal direction (toward the proximal portion 24 of the balloon catheter), the pull wire 74 also is moved in the proximal direction. The pull wire pulls the distal end of the steerable section 56 back toward the handle portion, thereby bending the steerable section and reducing its radius of curvature. The friction between the adjustment knob 70 and the slide nut 68 is sufficient to hold the pull wire taut, thus preserving the shape of the bend in the steerable section if the operator releases the adjustment knob 70. When the adjustment knob 70 is rotated in the opposite direction to move the slide nut 68 in the distal directions tension in the pull wire is released. The resiliency of the steerable section 56 causes the steerable to return its normal, non-deflected shape as tension on the pull wire is decreased. Because the pull wire 74 is not fixed to the slide nut 68, movement of the slide nut in the distal direction does not push on the end of the pull wire, causing it to buckle. Instead, the pin 80 is allowed to float within slot 82 of the slide nut 68 when the knob 70 is adjusted to reduce tension in the pull wire, preventing buckling of the pull wire.

In particular embodiments, the steerable section 56 in its non-deflected shape is slightly curved and in its fully curved position, the steerable section generally conforms to the shape of the aortic arch. In other embodiments, the steerable section can be substantially straight in its non-deflected position.

The handle portion 20 can also include a locking mechanism 84 that is configured to retain the balloon catheter 16 at selected longitudinal positions relative to the guide catheter 14. The locking mechanism 84 in the illustrated configuration comprises a push button 86 having an aperture 88 through which the outer shaft 26 of the balloon catheter extends. As best shown in FIG. 3A, the button 86 has a distal end portion 90 that is partially received in an internal slot 92. A coil spring 94 disposed in the slot 92 bears against and resiliently urges the distal end portion 90 toward the shaft 26. The distal end portion 90 can be formed with a small projection 96 that can nest within any of grooves 52a, 52b, 52c on the shaft 26 (FIG. 2A). When one of the grooves is aligned with the projection 96, the spring 94 urges the projection into the groove to retain the shaft 26 at that longitudinal position relative to the guide catheter (as depicted in FIG. 3A). Since the grooves in the illustrated embodiment extend circumferentially completely around the shaft 26, the balloon catheter can be rotated relative to the guide catheter when the longitudinal position of the balloon catheter is locked in place by the button 86. The position of the balloon catheter can be released by pressing inwardly on the button 86 against the bias of the spring 94 to remove the projection 96 from the corresponding groove on the shaft 26.

The handle portion 20 can have other configurations that are adapted to adjust the curvature of the steerable section 56. One such alternative handle configuration is shown co-pending U.S. patent application Ser. No. 11/152,288 (published under Publication No. US2007/0005131), which is incorporated herein by reference. Another embodiment of the handle portion is described below and shown in FIGS. 11-15.

FIGS. 7A and 7B show the guide catheter shaft 22 constructed in accordance with one specific embodiment. The shaft 22 in the illustrated embodiment comprises a tubular inner liner 104 made of a low-friction polymeric material, such as PTFE. The liner 104 is sized to allow a deflated balloon 28 and the balloon catheter shaft 26 to be inserted therethrough. A smaller conduit, or liner 106, which extends along the outside of the inner liner 104, defines a lumen through which the pull wire 74 extends. An outer layer 108 surrounds the liners 104, 106 and imparts the desired flexibility and stiffness to the shaft 22.

The outer layer 108 in the illustrated embodiment comprises a braided layer formed from braided metal wire 110 wound around the liner 104 and the conduit 106, and a polymeric material 112 surrounding and encapsulating the braided metal wire layer. In particular embodiments, the shaft can be formed by forming the liners 104, 106, placing the liners side-by-side in a parallel relationship relative to each other, wrapping the metal wire around the liners to form the braided layer, placing a polymeric sleeve over the braided layer, and reflowing the sleeve to form a uniform laminate layer 108 surrounding the liners. In certain embodiments, the polymeric material 112 comprises any suitable material, but desirably comprises a thermoplastic elastomer, such as Pebax®. The braided metal layer can be constructed from stainless steel wire.

As best shown in FIG. 7A, the shaft 22 desirably comprises a relatively stiff section 114 extending from the proximal end 116 of the shaft to the proximal end 118 of the steerable section 56. In particular embodiments, the length of the steerable section 56 comprises about ¼ of the overall length of the shaft 22. In a working embodiment, the overall length of the shaft 22 is about 45 inches (including the steerable section) and the length of the steerable section is about 11.7 inches, although the overall length of the shaft and/or the length of the steerable section can be varied depending on the particular application.

The steerable section 56 of the shaft desirably is formed from a relatively soft durometer material 112 to allow the steerable section to bend upon adjustment of the adjustment knob 70, as described above. The stiff section 114 desirably is formed from a relatively stiffer polymeric material 112 that resists bending when the pull wire is tensioned by the adjustment knob 70. The stiff section 114 desirably exhibits sufficient rigidity to allow the operator to push the apparatus 10 through a potentially constricting body vessel. In particular embodiments, the polymeric material 112 of the steerable section comprises 55D Pebax® and the polymeric material 112 of the remaining section 114 of the shaft comprises 72D Pebax®, which is stiffer than 55D Pebax®.

In alternative embodiments, the metal braided layer in the steerable section 56 can be replaced with a metal coil (e.g., a stainless steel coil) disposed on the inner liner 104 to enhance the flexibility of the steerable section. Thus, in this alternative embodiment, the braided metal layer extends along the stiff section 114 and the metal coil extends along the steerable section 56. In another embodiment, the metal braided layer in the steerable section 56 can be replaced with a stainless steel hypotube that is formed with laser-cut, circumferentially extending openings, such as disclosed in co-pending U.S. patent application Ser. No. 11/152,288.

As shown in FIG. 7C, the distal end of the shaft 22 can include a flared, or enlarged, end portion 116. The outer diameter D of the end portion 116 is equal to or about the same as the outer diameter of the crimped valve 12 supported on the balloon 28. Accordingly, when the valve 12 is advanced through an introducer sheath, the end portion 116 pushes against the crimped valve 12, rather than the balloon 28. This minimizes inadvertent movement between the balloon catheter and the valve, which can cause the position of the valve on the balloon to move. In particular embodiments, the shaft 22 has an outer diameter of about 16 F to about 18 F and the end portion 116 has an outer diameter D of about 22 F. The enlarged end portion 116 can be made of any of various suitable materials. For example, the end portion 116 can be molded from Pebax® (e.g., 55D Pebax®) and reflowed on the end portion of the steerable section 56.

As mentioned above, the distal end of the pull wire 74 is secured at the distal end of the steerable section 56. As best shown in FIG. 7C, this can be achieved by securing the distal end portion of the pull wire 74 to a metal ring 118 embedded in the outer layer 108 of the shaft, such as by welding the pull wire to the metal ring.

Although not shown in FIGS. 7A-7C, the guide catheter shaft 22 can include a cover 23 for covering the valve 12 and the balloon 28 (or a portion thereof) during delivery of the valve. As explained below, the use of an introducer sheath can be optional if the valve is covered upon insertion into the patient's vasculature.

Referring to FIGS. 4A and 4B, and as discussed briefly above, the nose catheter 18 includes an adjustment ring 50 at its proximal end and a nose piece 32 at its distal end, and an elongated shaft 30 extending therebetween. The shaft 30 desirably is formed with a lumen 120 extending the length of the shaft for receiving a guide wire 140 (FIG. 8A) so that the apparatus 10 can be advanced over the guide wire after it is inserted into the delivery path in the body. As shown in FIGS. 4A and 4B, the nose piece 32 desirably is formed with an opening or cavity 122 sized and shaped to receive at least a distal end portion of the balloon 28.

As best shown in FIG. 4A, the adjustment ring 50 is disposed on and slidable relative to the slide support 48 of the balloon catheter, which function as a locking or retaining mechanism for retaining the nose catheter at selective longitudinal positions relative to the balloon catheter. Explaining further, the shaft 30 extends through and is fixedly secured to a shaft support 124 disposed within the side support 48. The adjustment ring 50 is secured to the shaft support 124 by screws 126, which extend through elongated slots 128a, 128b in the slide support 48. Slots 128a, 128b extend longitudinally along the length of the slide support 48. Hence, when the adjustment ring 50 is slid longitudinally along the length of the slide support 48 (in the directions indicated by double-headed arrow 130), the shaft support 124 and the shaft 30 are caused to move in the same direction so as to adjust the longitudinal position of the nose catheter relative to the balloon catheter.

The slot 128a is formed with circumferentially extending notches 132a-132d and the slot 128b is formed with similar circumferentially extending notches 134a-134d opposite the notches 132a-132d. Thus, for each notch 132a-132d, there is a corresponding, diametrically opposed notch 134a-134d extending from slot 128b. To retain the longitudinal position of the nose catheter relative to the balloon catheter, the adjustment ring 50 is moved to align the screws 126 with a pair of diametrically opposed notches and then rotated slightly to position the screws 126 in the notches. For example, FIG. 4A shows the screws 126 positioned in notches 132b and 134b. The notches restrict movement of the screws 126, and therefore the shaft support 124 and the shaft 30, in the distal and proximal directions.

In the illustrated embodiment, each slot 128a, 128b is formed with four notches. When the screws 126 are positioned in notches 132c, 134c or in notches 132d, 134d, the nose piece 32 is retained at a position covering a distal end portion of the balloon 28 and abutting the cover 23 of the guide catheter 14 such that the balloon 28 and the valve 12 are completely enclosed by the cover 23 and the nose piece 32 (FIG. 8A). When the screws 126 are positioned in notches 132b, 134b, the nose piece 32 is retained at a position spaced distally a first distance from the balloon 28 so that the valve can be deployed by inflating the balloon without inference from the nose piece (FIG. 8C). When the screws are positioned in notches 132a, 134a, the nose piece is retained at a position spaced distally a second distance, greater than the first distance, from the balloon 28. In this position, the balloon 28 can be refolded inside the cover 23 (after valve deployment) without interference from the nose piece.

The valve 12 can take a variety of different forms. In particular embodiments, the valve generally comprises an expandable stent portion that supports a valve structure. The stent portion desirably has sufficient radial strength to hold the valve at the treatment site and resist recoil of the stenotic native valve leaflets. Additional details regarding balloon expandable valve embodiments can be found in U.S. Pat. Nos. 6,730,118 and 6,893,460, each entitled IMPLANTABLE PROSTHETIC VALVE, which are incorporated by reference herein. It will also be appreciated that the delivery system may be used with self-expanding prosthetic valves. For example, when using a self-expanding valve, a pusher may be used to assist in ejecting the self-expanding valve from a delivery sleeve that maintains the valve in its compressed state.

When the valve 12 is used to replace the native aortic valve (or a previously implanted, failing prosthetic aortic valve), the valve 12 can be implanted in a retrograde approach where the valve, mounted on the balloon in a crimped state, is introduced into the body via the femoral artery and advanced through the aortic arch to the heart. In use, a guide wire 140 (FIG. 8A) can be used to assist in advancing the delivery device 10 through the patient's vasculature. The guide wire 140 can be placed in the body vessel through a dilator (not shown), which expands the inner diameter of the body vessel for introducing the delivery device. Dilator diameters range between, for example, 12 and 22 French.

As noted above, and as shown in FIG. 8A, the valve 12 can be positioned inside the cover 23 with the nose piece 32 covering the distal end portion of the balloon 28 and abutting the distal end of the cover 23. The adjustment ring 50 of the nose catheter can be locked in place to retain nose piece 32 against the cover 23 during delivery. In this position, the nose catheter desirably is placed in slight tension with the nose piece 32 held tightly against the cover 32 to inhibit separation of the nose piece from the cover while tracking the device through the vasculature and during removal of the delivery apparatus from the body.

Advantageously, because the valve 12 in the illustrated embodiment can be completely covered by the cover 23, an introducer sheath is not needed to introduce the valve into the body vessel. An introducer sheath having a diameter of about 22 to 24 French typically is used in a retrograde procedure. In contrast, the cover 23 desirably has an outer diameter that is less than the outer diameter of the introducer sheath, and in particular embodiments, the outer diameter of the cover 23 is in the range of about 0.260 inch to about 0.360 inch, with about 0.330 inch being a specific example. By reducing the overall diameter of the device, it is less occlusive to the femoral artery and the patient's leg can remain well perfused during the procedure. Further, because the cover 23, which represents the largest diameter of the delivery device, need only be in contact with the femoral and iliac arteries for only a very short period of time, trauma to these vessels can be minimized.

Although less desirable, in other embodiments the cover 23 can be shorter in length so that less of the outer surface of the valve and the balloon is covered by the cover 23 during delivery. For example, the cover 23 can be dimensioned to extend over only a proximal end portion of the balloon or a proximal end portion of the valve.

As the delivery apparatus 10 is advanced over the guide wire 140 and through the aortic arch, the guide catheter 14 is used to "steer" the apparatus away from the inner surface of the aorta. The tapered distal end portion of the nose piece 32 assists in tracking through the femoral and iliac arteries, as well as provides atraumatic tracking through over the aortic arch and smooth crossing of the native aortic valve. In prior delivery systems, it is known to fix a nose piece at the distal end of the balloon catheter, which increases the length of the portion of the device that cannot be curved by operation of a guide catheter. In contrast, the nose piece 32 in the illustrated embodiment is mounted on separate nose catheter 18 that can be moved relative to the valve 12. The nose piece 32 therefore can be mounted over the distal end portion of the balloon during delivery in order to minimize the length of the non-steerable section at the distal end of the delivery device. This allows for easier tracking through the aortic arch with little or no contact between the end of the delivery device and the inner walls of the aorta. In particular embodiments, the length L (FIG. 8A) of the non-steerable section at the end of the delivery device is about 6 cm or less.

Using conventional fluoroscopy, the operator can track the positions of marker bands 142 (FIGS. 2A and 2B) on the guide wire shaft 34 in order to position the valve at the implantation site. After the valve 12 is advanced into the aortic annulus, the nose catheter can be moved distally relative to the balloon catheter to advance the nose piece 32 distally away from the balloon 28 (FIG. 8B) and the guide catheter can be moved proximally relative to the balloon catheter to expose the valve 12 from the cover 23 (FIG. 8C). As explained above, the longitudinal positions of the nose catheter and the guide catheter can be fixed relative to the balloon catheter while the operator adjusts the position of and then deploys the valve 12. Inflation of the balloon 28 is effective to expand the valve 12 to engage the native valve leaflets. The balloon 28 can then be deflated and retracted back into the cover 23 and the nose piece 32 can be pulled back over the distal end portion of the balloon. The entire delivery apparatus can then withdrawn back over the guide wire 140 and removed from the body, after which the guide wire can be removed from the body.

Figure 9:
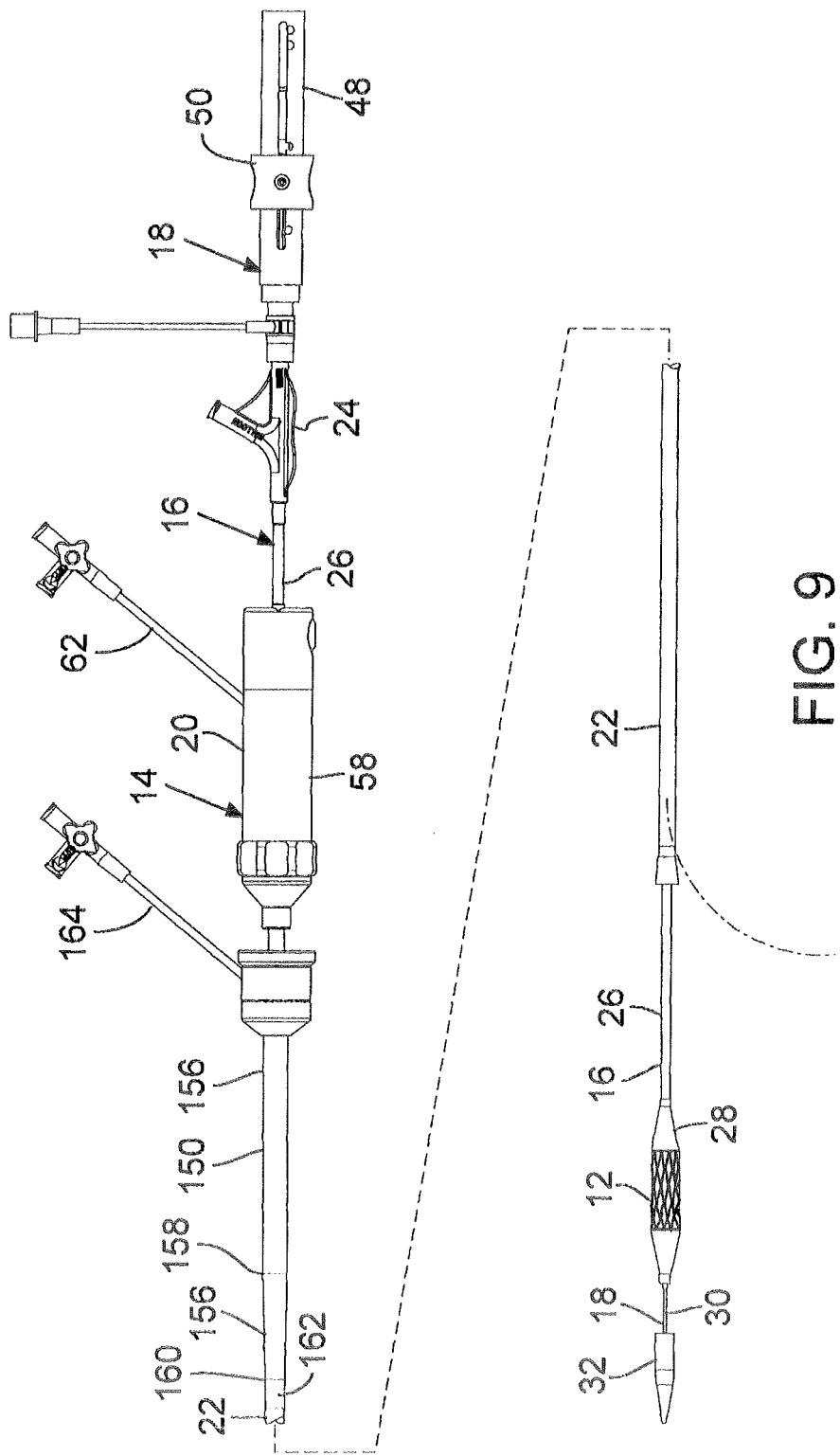
FIG. 9 is side view of an endovascular delivery apparatus for implanting a prosthetic valve, according to another embodiment.
Figure 10B:
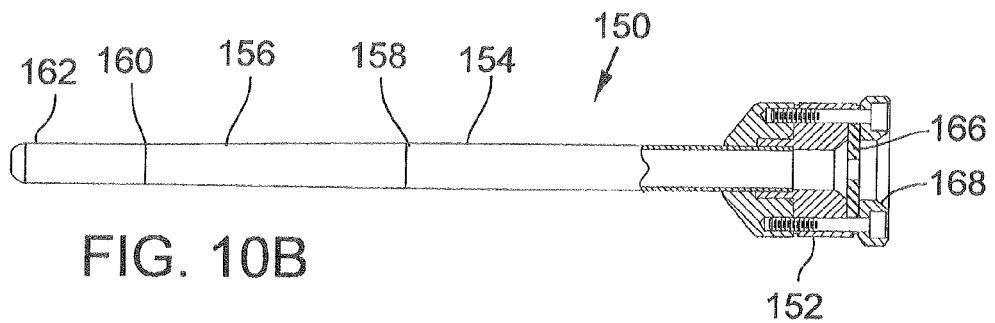
FIG. 10B is a side view of the introducer sheath of FIG. 10A shown partially in section.
Figure 10A:
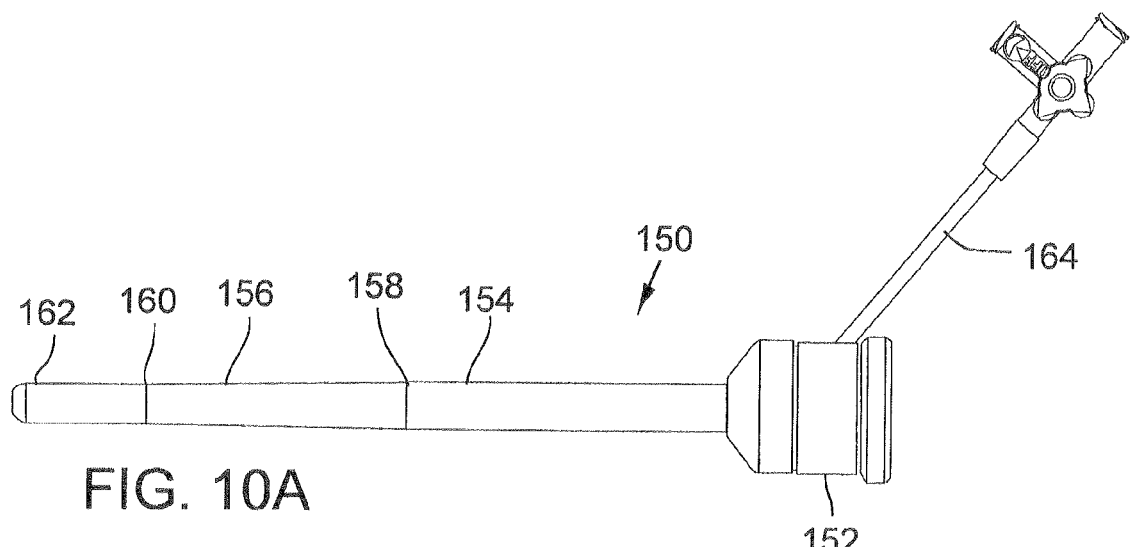
FIG. 10A is a side view of the introducer sheath of the deliver apparatus shown in FIG. 9.
Figure 10C:
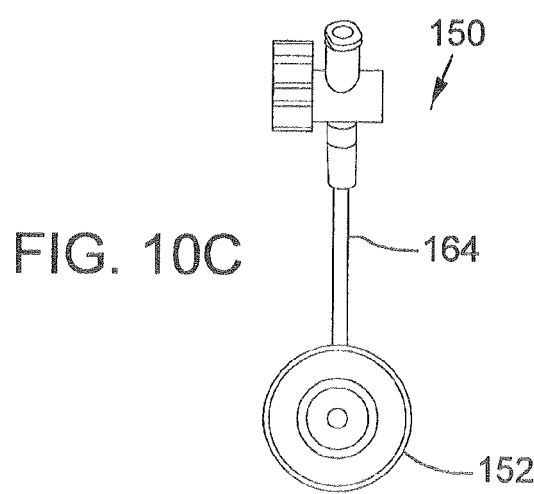
FIG. 10C is an end view of the introducer sheath of FIG. 10A.

FIG. 9 shows an alternative embodiment of the delivery apparatus 10. In this embodiment, the guide catheter 14 is not provided with a cover 23 (as previously illustrated in FIGS. 3A and 3B) and instead an introducer sheath 150 can be used to introduce the delivery apparatus into the body. As best shown in FIGS. 10A and 10B, the introducer sheath 150 in the illustrated embodiment includes an introducer housing 152 and an introducer sleeve 154 extending from the housing 152. The housing 152 houses a sealing valve 166. In use, the sleeve 154 is inserted into a body vessel (e.g., the femoral artery) while the housing 152 remains outside the body. The delivery apparatus 10 is inserted through a proximal opening 168 in the housing, the sealing valve 166, the sleeve 154 and into the body vessel. The sealing valve 166 sealingly engages the outer surface of the guide catheter shaft 22 to minimize blood loss. In certain embodiments, the sleeve 154 can be coated with a hydrophilic coating and extends into the body vessel about 9 inches, just past the iliac bifurcation and into the abdominal aorta of the patient.

The sleeve 154 can have a tapered section 156 that tapers from a first diameter at a proximal end 158 to a second, smaller diameter at a distal end 160. A reduced diameter distal end portion 162 extends from the tapered portion 156 to the distal end of the sleeve 154. The tapered portion 156 provides for a smoother transition between the outer surface of the sleeve 154 and the outer surface of the guide shaft 22 of the guide catheter 14. The tapered portion 156 also allows for variable placement of the sleeve 154 in the patient's vasculature to help minimize complete occlusion of the femoral artery.

FIGS. 11-15 show an alternative embodiment of a handle portion, indicated at 200, that can be used in the guide catheter 14 (FIGS. 1 and 3A), in lieu of handle portion 20. The handle portion 200 in the illustrated embodiment includes a main housing 202 and an adjustment lever 204 pivotably connected to the housing 202. The lever 204 can be pivoted distally and proximally (as indicated by double-headed arrow 206 in FIG. 13) to adjust the curvature of the shaft 22, as further described below.

Figure 11:
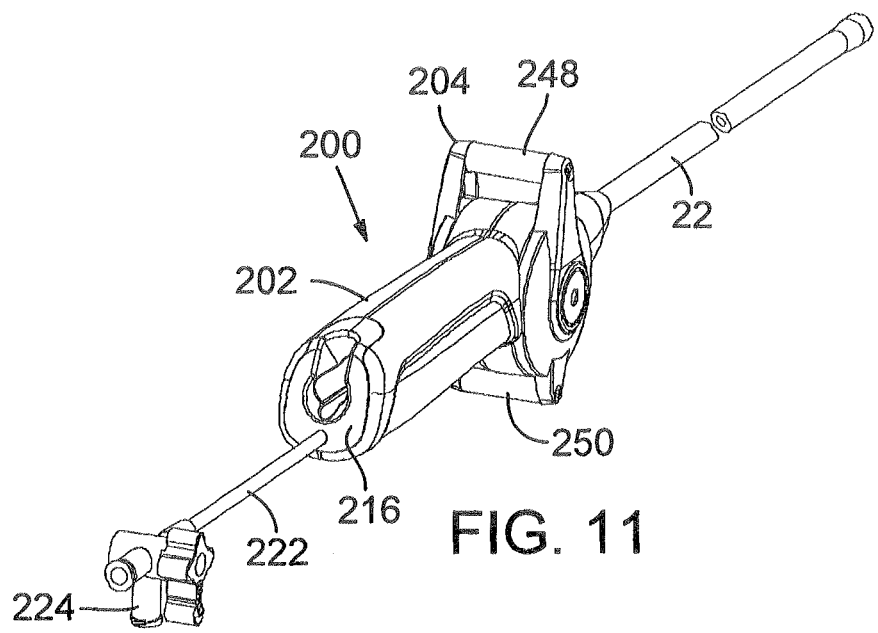
FIG. 11 is a perspective view of an alternative embodiment of a guide catheter.
Figure 12:
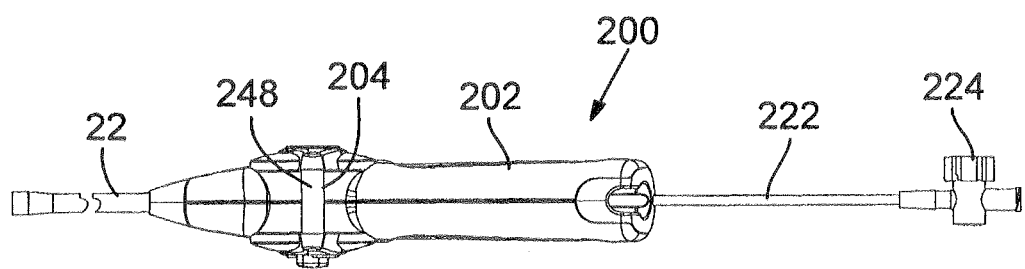
FIG. 12 is a top plan view of the guide catheter of FIG. 11.
Figure 13:
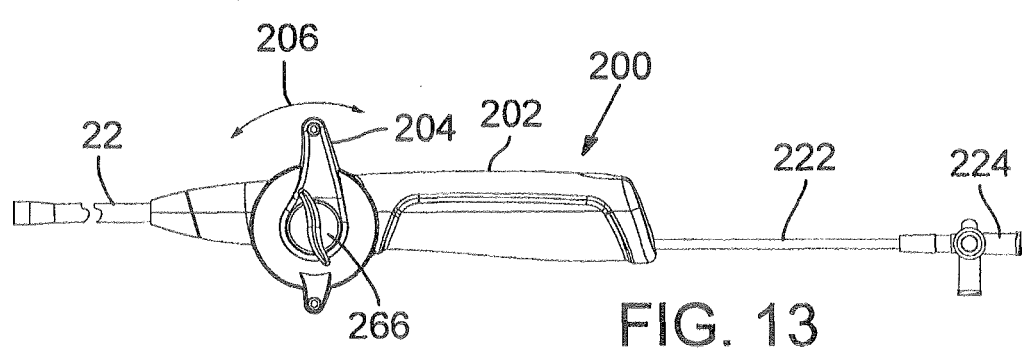
FIG. 13 is a side elevation view of the guide catheter of FIG. 11.
Figure 14:
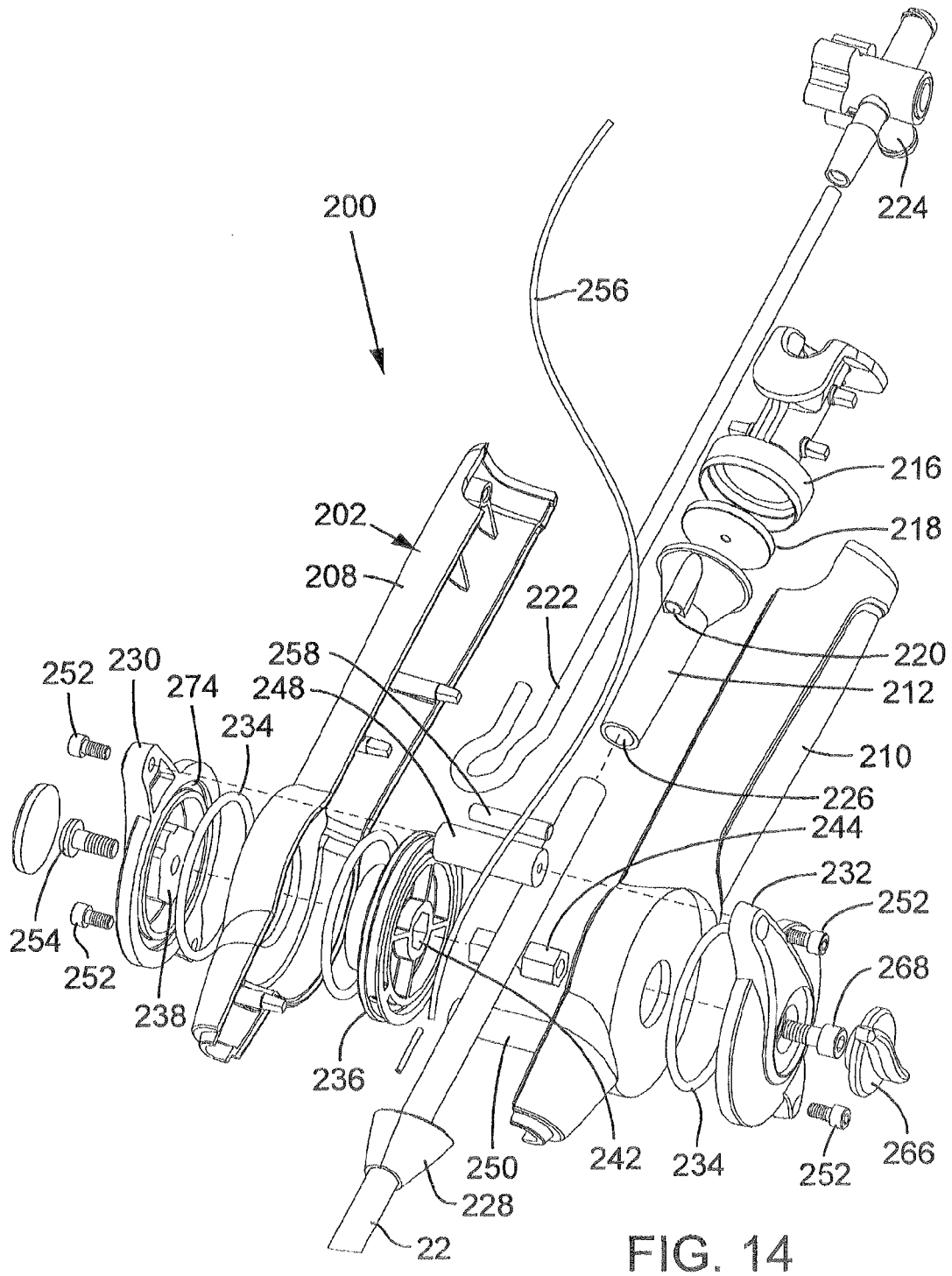
FIG. 14 is a perspective, exploded view of the guide catheter of FIG. 11.
Figure 15:
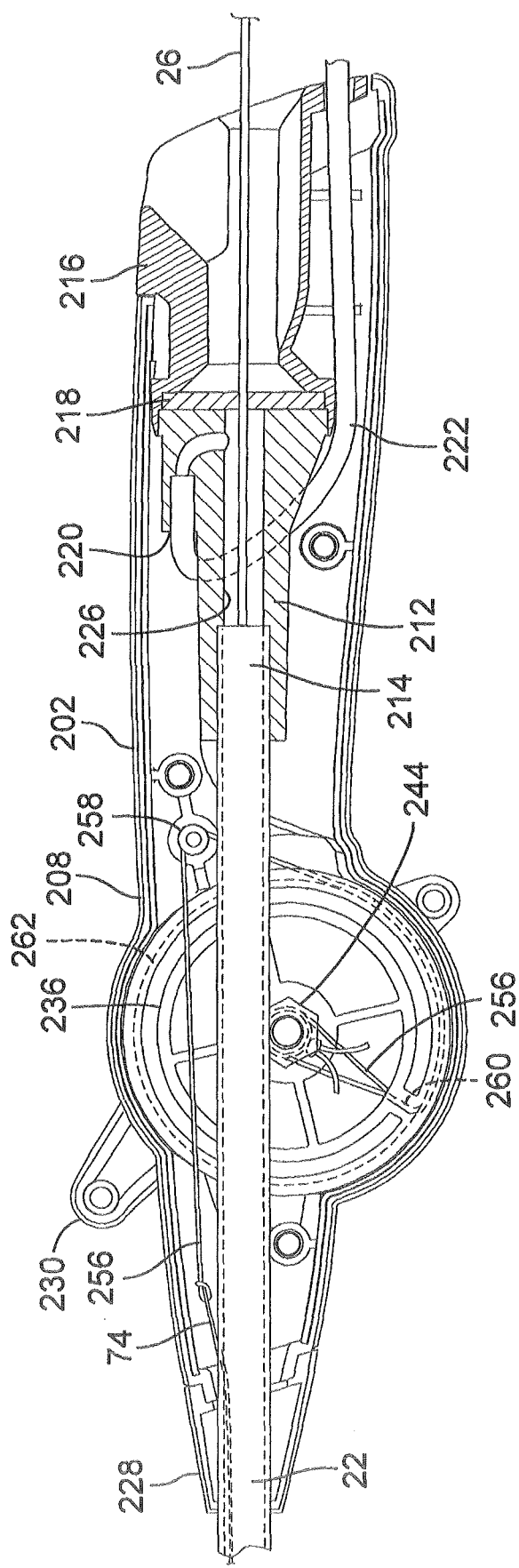
FIG. 15 is a partial, cross-sectional view of the guide catheter of FIG. 11.

As best shown in FIG. 14, the housing 202 can be formed from first and second housing portions 208, 210 that can be secured to each other using a suitable adhesive, mechanical fasteners, a snap fit connection, or other suitable techniques. Disposed within the housing 202 is a seal housing 212 that has a central bore 226 extending therethrough. The distal end portion of the bore 226 can form an enlarged portion that receives the proximal end portion 214 of the shaft 22. The shaft 22 extends from the seal housing 212 through the main housing 202 and out of a nose piece 228 connected to the distal end of the main body 202. An end piece 216 can be connected to the proximal end of the seal housing 212 with a seal 218 captured between these two components. As best shown in FIG. 15, the end piece 216 can be formed with a stepped bore shaped to receive the seal 218 and an end portion of the seal housing 212. The seal 218 can be made of a suitable elastomer, such as silicon. The shaft 26 of the balloon catheter 16 extends through the end piece 216, a central opening in the seal 218, the seal housing 212, and the guide catheter shaft 22. The seal housing 212 can be formed with a flush port 220 that is in fluid communication with the central bore 226. The flush port 220 receives one end of a flexible tube 222. The opposite end of the tube 222 can be connected to a stopcock 224 (FIG. 11).

As shown in FIG. 14, the lever 204 in the illustrated configuration comprises first and second lever portions 230, 232, respectively, mounted on opposite sides of the main housing 202. The inner surface of each lever portion can be formed with an annular groove 274 adapted to receive a respective O-ring 234. The lever portion 230 can be coupled to a pulley 236 mounted in the housing to produce rotation of the pulley upon pivoting movement of the lever portion. For example, the lever portion 230 can be formed with a projection 238 that extends through the housing portion 208 and into a complementary shaped recess 240 (FIG. 16A) in the pulley 236. The projection 236 can be formed with flats on its outer surface that engage corresponding flats in the recess 240 to produce rotation of the pulley when the lever is activated. The pulley 236 can also be formed with a non-circular recess or opening 242 that is shaped to receive one end portion of a shaft 244 (FIG. 14). The opposite end of the shaft 244 extends through the second housing portion 210 and into a complementary shaped recess or opening 246 of the lever portion 232 (FIG. 17). In the illustrated configuration, the end portions of the shaft 244 and the corresponding openings 242 and 246 are hexagonal to inhibit relative rotation between the shaft 244, the pulley 236, and the lever portion 232, although various other non-circular shapes can be used. Alternatively, the end portions of the shaft and the openings 242, 246 can be circular if the shaft is otherwise fixed against rotation relative to the pulley and the lever portion.

Upper and lower cross-bars 248, 250, respectively, are connected to and extend between respective upper and lower ears of the first and second lever portions 230, 232. Screws 252 extending through the ears of the lever portions 230, 232 and tightened into the cross-bars 248, 250 can be used to secure the components of the lever 204 to the main body 202. A screw 254 can extend through the lever portion 230, the housing portion 208, and into a threaded opening in the shaft 244. An adjustment knob 266 can be fixedly secured to a screw 268, which can extend through the lever portion 232, the housing portion 210, and into a threaded opening in the opposite end of the shaft 244. The screw 268 can be fixedly secured to the adjustment knob, for example, by adhesively securing the head of the screw within a recess (not shown) on the inner surface of the adjustment knob. Consequently, the adjustment knob 266 can be manually rotated to loosen or tighten the screw into the shaft 244 to adjust the rotational friction of the pulley 236.

Referring again to FIG. 15, a pull wire 74 extends through a pull wire lumen in the shaft 22 and extends from the shaft inside of the main housing 202. A flexible tension member 256, such as a piece of string, is tied off or otherwise connected to at one thereof to the end of the pull wire 74. The tension member 256 extends around a cross-member 258, partially around the outer circumference of the pulley 236, through a radially extending opening 260 in the pulley and is tied off or otherwise connected to the shaft 244 adjacent the center of the pulley 236. As shown in FIGS. 16A and 16B, the pulley 236 can be formed with an annular groove or recess 262 adapted to receive the tension member 256.

Figure 18A:
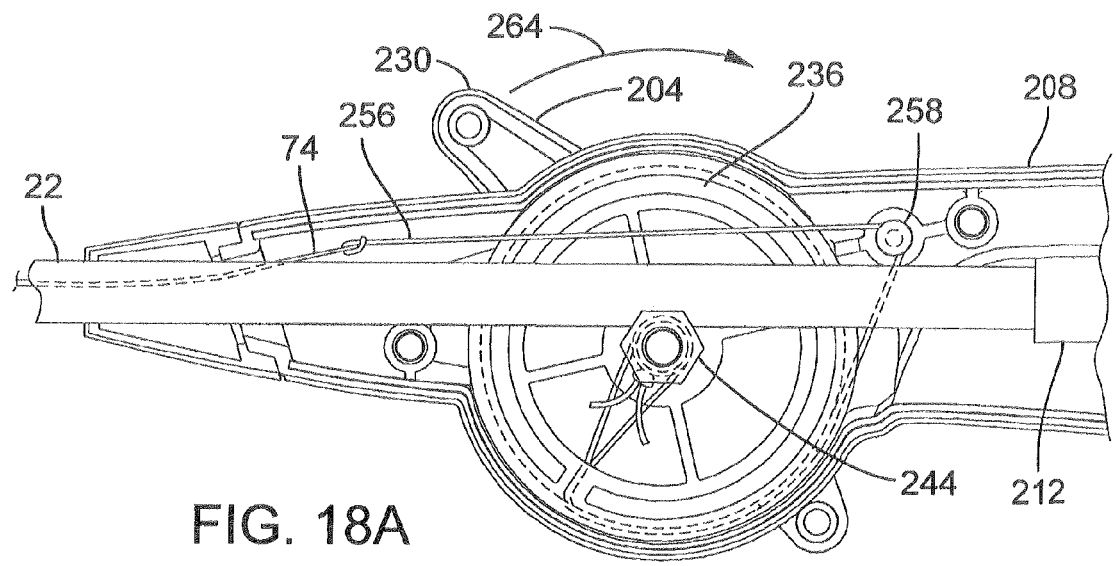
FIGS. 18A and 18B are partial, cross-sectional views of the guide catheter of FIG. 11 illustrating the operation of an adjustable lever for adjusting the curvature of the guide catheter.
Figure 18B:
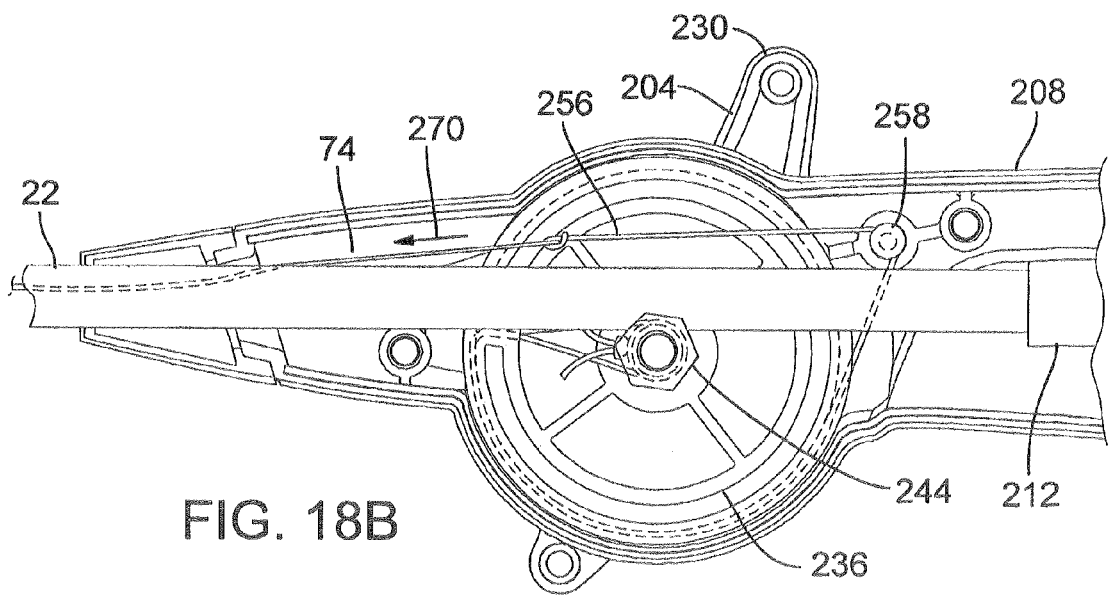

Explaining the operation of the handle portion 200, FIG. 18A shows the adjustment lever 204 in a forward-most position. In this position, the steerable section 56 of the shaft 22 is in its normal, non-deflected state (e.g., straight, such as shown in FIG. 1, or slightly curved). As the lever 204 is pivoted rearwardly, in the direction of arrow 264, the pulley 236 is rotated clockwise in the illustrated embodiment, causing the tension member to wind around the pulley and pull the pull wire 74 rearwardly. The pull wire 74, in turn, pulls on the distal end of the shaft to adjust the curvature of the steerable section 56, in the manner previously described. FIG. 18B shows the lever 204 in a rearward-most position corresponding to the fully curved position of the steerable section of the shaft 22.

The rotational friction of the pulley 236 is sufficient to hold the pull wire taut, thus preserving the shape of the bend in the steerable section if the operator releases the adjustment lever 204. When the lever 204 is pivoted back toward the forward-most position (FIG. 18A), tension in the pull wire is released. The resiliency of the steerable section 56 causes the steerable section to return to its normal, non-deflected shape as tension on the pull wire is released. Because the tension member 256 in the illustrated embodiment does not apply a pushing force to the pull wire, movement of the lever 204 toward the forward-most position does not cause buckling of the pull wire. Further, as noted above, the adjustment knob 266 can be adjusted by the operator to vary the rotational friction of the pulley 236. The rotational friction desirably is adjusted such that if the guide catheter is pulled back inadvertently while in the patient's vasculature, the pulley can rotate toward the forward-most position under a forward pulling force of the pull wire (as indicated by arrow 270 in FIG. 18B) to allow the steerable section to straighten out as it is pulled through the vasculature, minimizing trauma to the vasculature walls.

Advantageously, the adjustment lever 204 in the illustrated embodiment provides a substantially 1:1 deflection of the steerable section in response to movement of the lever; that is, rotation of the lever 204 causes a substantially 1:1 movement of the pull wire and therefore the steerable section 56. In this manner, the adjustment lever 204 provides the operator tactile feedback of the curvature of the steerable section to facilitate tracking through the vasculature. In addition, the lever is ergonomically positioned for maintaining the proper orientation of the guide catheter during use. Another advantage of the illustrated handle portion 200 is that the proximal portion 24 of the balloon catheter 16 (FIG. 2B) or a portion thereof can seat within the end piece 216 to minimize the working length of the balloon catheter.

Figure 19A:
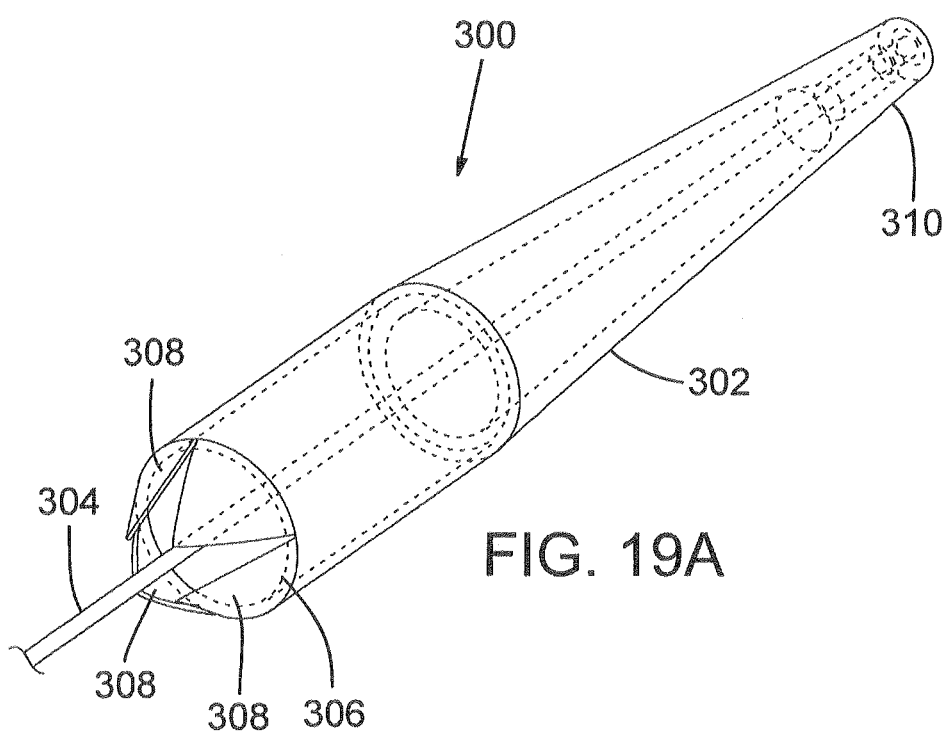
FIG. 19A is a perspective view of the distal end portion of alternative embodiment of a nose catheter.

FIGS. 19A and 19B illustrate an alternative nose catheter 300, according to one embodiment, that can be used with the delivery apparatus 10 (FIG. 1), in lieu of the nose catheter 18. The nose catheter 300 in the illustrated configuration includes a nose piece or valve cover 302 connected to a nose catheter shaft 304. The valve cover 302 is adapted to cover the balloon 28 and a valve 12 mounted on the balloon. Thus, in this embodiment, the guide catheter 14 need not have a cover 23 (FIG. 8A) to cover the valve during delivery. The shaft 304 is fixedly secured at its distal end to the distal end of the cover 302 and extends through the balloon 28 and the balloon catheter shaft 26. The shaft 304 can have a lumen to receive a guide wire 140. The shaft 304 can move longitudinally relative to the balloon catheter and the guide catheter, much like the nose catheter 18 previously described.

As best shown in FIG. 19A, the cover 302 has a proximal end portion 306 formed with a plurality of slits defining triangular flaps 308. The flaps 308 can flex radially outwardly from each other to form an opening large enough to allow passage of the balloon 28 and the valve 12 when it is desired to deploy the valve. The proximal end portion 306 can be tapered as shown to facilitate retraction of the cover 302 back into an introducer sheath. The tapered shape of the end portion 306 also provides an atraumatic surface to minimize trauma to the vasculature walls when the delivery apparatus is withdrawn from the body. The cover also can have a tapered distal end portion 310 to assist in tracking through the femoral and iliac arteries, as well as provide atraumatic tracking through the aortic arch and smooth crossing of the native aortic valve.

The cover 302 desirably is made from a flexible material, such as nylon, Pebax®, or PET and can have a wall thickness in the range of about 0.0015 inch to about 0.015 inch. By making the cover 302 sufficiently flexible, the only relatively stiff, non-flexible section along the portion of the delivery apparatus advanced through the patient's vasculature is the section of the balloon covered by the valve. This greatly enhances the ability of the delivery apparatus to follow the path of the guide wire 140 as it is advanced through tortuous body vessels.

In use, the delivery apparatus is advanced over the guide wire 140 until the valve is positioned at or near the deployment location. The nose catheter 300 is then advanced distally relative to the balloon catheter 16 to uncover the balloon and the valve 12, as illustrated in FIG. 19C. As the cover 302 is advanced distally, the balloon and the valve can pass through the proximal opening formed by flaps 308. Once the valve 12 is exposed, the balloon 28 can be inflated to deploy the valve.

Figure 20A:
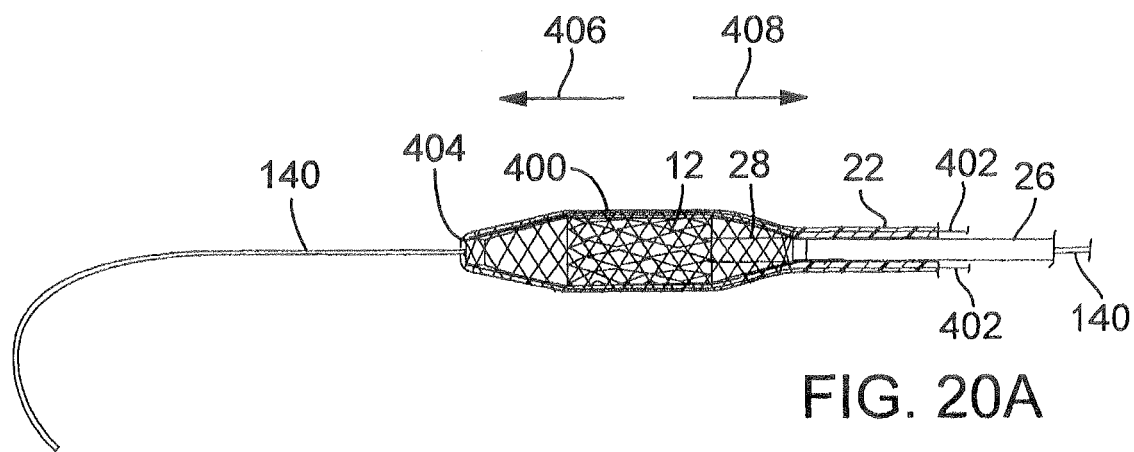
FIG. 20A is a side elevation view of the distal end portion of a delivery apparatus, according to another embodiment.

FIG. 20A shows a modification of the guide catheter 14 where the valve cover 23 is replaced with an expandable mesh basket or cover 400 connected to the distal end of the guide catheter shaft 22. The cover 400 is sized and shaped to cover the valve 12 and the balloon 28. Thus, in this embodiment, a nose catheter (e.g., nose catheter 18) need not be used. The cover 400 can have a braided mesh construction formed from metal wire (e.g., Nitinol or stainless steel wires).

Figure 20B:
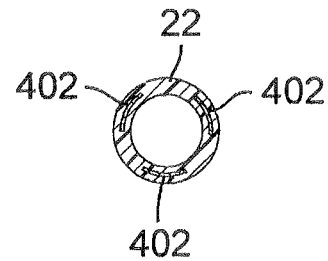
FIG. 20B is a transverse cross-sectional view of the guide catheter of the delivery apparatus of FIG. 20A.

One or more ribbon wires 402 are connected to the distal end 404 of the cover 400 and extend through respective lumens in the guide catheter shaft 22 along the length thereof (FIG. 20B). The wires 402 can be, for example, 0.003 inch× 0.020 inch Nitinol ribbon wire. The wires 402 are connected at their proximal ends to a handle portion of the guide catheter that allows the operator to apply pushing or pulling forces to the wires. Pushing the wires 402 forward, in the direction of arrow 406, causes the cover to collapse over the balloon 28 and the valve 12 to provide a smooth tracking profile. Pulling the wires 402 rearward, in the direction of arrow 408, causes the cover to expand and allows the balloon and valve to be advanced outwardly through an opening at the distal end 404 of the cover 400.

In use, the cover 400 is placed in a collapsed state covering the valve and the balloon for delivery through the patient's vasculature to the deployment site. The wires 402 are then pulled in the proximal direction (as indicted by arrow 408) to expand the cover 400. The guide catheter can then be pulled in the proximal direction to advance the balloon and the valve from the distal end of the cover. Alternatively, the balloon catheter 16 can be advanced distally relative to the guide catheter 14 to advance the balloon and the valve from the cover 400.

FIGS. 21A-21C show an alternative embodiment of a delivery apparatus, indicated at 500. The delivery apparatus 500 allows a valve 12 to be mounted on a balloon 28 of a balloon catheter inside a body vessel. The balloon catheter can have a construction similar to the balloon catheter shown in FIGS. 2A and 2B except that in the embodiment of FIGS. 21A-21B, the balloon catheter shaft 26 has a distal end portion 504 that extends distally from the balloon 28 and an annular tapered wedge 502 is disposed on the distal end portion 504 adjacent the balloon. The tapered wedge 502 functions to expand the valve to facilitate positioning the same on the balloon inside the body, as further described below. The wedge 502 desirably is made from a low-friction material, such as nylon, to allow the valve to easily slide over the wedge and onto the balloon.

The delivery apparatus includes a nose catheter comprising a shaft 506 and a nose piece 508 connected to the distal end of the shaft 506. The nose catheter shaft 506 can have a guide wire lumen to receive a guide wire 140 so that the apparatus can be advanced over the guide wire with the guide wire passing through the lumen. The delivery apparatus 500 can further include a guide catheter comprising a guide catheter shaft 22 and an elongated cover 510 extending from the distal end of the shaft 22. The nose catheter, balloon catheter, and guide catheter are moveable longitudinally relative to each other and can have locking mechanisms at the proximal end of the apparatus for retaining the catheters at selected longitudinal positions relative to each other, as described in detail above.

As shown in FIG. 21A, the valve 12 is initially mounted in a crimped state on the nose catheter shaft 506 between the nose piece 508 and the tapered wedge 502, rather than on the balloon prior to inserting the delivery apparatus into the body. The valve is crimped onto the nose catheter shaft such that that valve can still move along the shaft when it is desired to place the valve on the balloon 28. The nose piece 508 can be formed with a stepped bore comprising a first bore portion 512 and a second, enlarged bore portion 514 at the proximal end of the nose piece. The stepped bore can be formed with an annular shoulder 516 extending between the first and second bore portions and adapted to engage the distal end of the valve 12 when the valve is inserted into the second portion 514. The nose piece 508 can have an outer surface that tapers in a direction toward the distal end of the nose piece 508 to provide atraumatic tracking through tortuous vasculature. The cover 510 which can be optional, is adapted to extend over and cover the balloon 28, the wedge 502, and at least a proximal end portion of the valve 12 when the valve is positioned on the nose catheter shaft for delivery. In the illustrated embodiment, the distal end of the cover 510 can be positioned to abut the proximal end of the nose piece 508 so as to completely enclose the valve during delivery. In alternative embodiments, the cover 510 can be shorter in length so that less of the outer surface of the valve or the balloon is covered during delivery.

The nose piece 508, when moved proximally relative to the balloon catheter (in the direction indicated by arrow 518), pushes the valve 12 over the wedge 502 and onto the balloon 28. As the valve passes over the wedge, the valve expands slightly to facilitate positioning the same on the balloon. The balloon catheter shaft 26 can have radiopaque markers 520 (FIG. 21A) to assist the operator in aligning the valve at the proper location on the balloon. The nose piece can have an outer layer 522 formed from a relatively soft and flexible material and an inner layer 524 formed from a relatively harder material. The inner layer 524 in the illustrated embodiment forms the shoulder 516 and the inner surface of the first bore portion 512. In this manner, the nose piece exhibits sufficient rigidity to push the valve 12 over the wedge and onto the balloon and provides a soft outer surface to minimize trauma to the body vessels. For example, the outer layer 522 can be made of 55D Pebax® and the inner layer can be made of 72D Pebax®, which is stiffer than 55D Pebax®.

The section of the delivery apparatus mounting the valve typically defines the maximum outer diameter of the apparatus inserted into the body. By mounting the valve 12 on the nose catheter shaft rather than on the balloon prior to insertion into the body, the valve 12 can be crimped to a smaller diameter than if the valve is mounted on the balloon. Accordingly, the maximum outer diameter of the delivery apparatus can be reduced for insertion into and through the vasculature. As noted above, by reducing the maximum diameter of the delivery apparatus, it is less occlusive to the femoral artery and therefore the patient's leg can remain well perfused during the procedure. In certain embodiments, the maximum outer diameter of the cover 510 and the nose piece 508 (at its proximal end) is about 0.223 inch, which is the maximum diameter of the portion of the delivery apparatus that is inserted into the body. The wedge 502 can have a diameter at its proximal end of about 0.120 inch and the guide catheter shaft 22 can have an outer diameter of about 0.184 inch.

Explaining now the operation of the delivery apparatus 500, according to one embodiment, the valve 12 is initially mounted on the nose catheter shaft and inserted into the nose piece 508 and the cover 510. After a guide wire 140 is inserted into the body, the proximal end of the wire extending from the body can be inserted into the distal end of the guide wire lumen and the delivery apparatus 500 can be inserted into a body vessel (e.g., the femoral artery) and advanced through the body (as depicted in FIG. 21A). Alternatively, an introducer sheath can be inserted first into the body vessel, for example if a cover 510 is not provided to cover the valve 12. Subsequent to inserting the introducer sheath, the delivery apparatus can be inserted through the introducer sheath and into the body vessel.

When the distal end of the delivery apparatus is advanced to a location that is convenient to slide the valve 12 onto the balloon, the guide catheter is retracted proximally relative to the balloon catheter to advance the valve and the balloon from the cover 510. For example, if implanting a prosthetic valve within the native aortic valve, the valve and the balloon can be advanced into the ascending aorta or into the left ventricle where the valve can then be moved onto the balloon. In any case, as shown in FIG. 21B, the nose catheter can be retracted proximally to advance the valve over the wedge 502 and onto the balloon 28. Markers 520 (FIG. 21A) can be used to center the valve on the balloon. After mounting the valve on the balloon, the nose catheter can be advanced distally so as not to interfere with inflation of the balloon, as shown in FIG. 21C. The valve can then be positioned at the implantation site (e.g., within the native aortic valve) and deployed by inflating the balloon.

FIGS. 22A and 22B show a modification of the delivery apparatus 10 (FIGS. 1-8). In the embodiment of FIGS. 22A and 22B, the cover 23 has a generally tubular shape but is provided in a rolled up state on the distal end portion of the guide catheter shaft 22. After the valve 12 is mounted on the balloon 28, the cover can be unrolled over the valve 12 for insertion into and through the patient's vasculature. The operation of the deliver apparatus shown in FIGS. 22A and 22B is otherwise identical to the operation of the delivery apparatus 10 described above with reference to FIGS. 8A-8C.

Figure 23A:
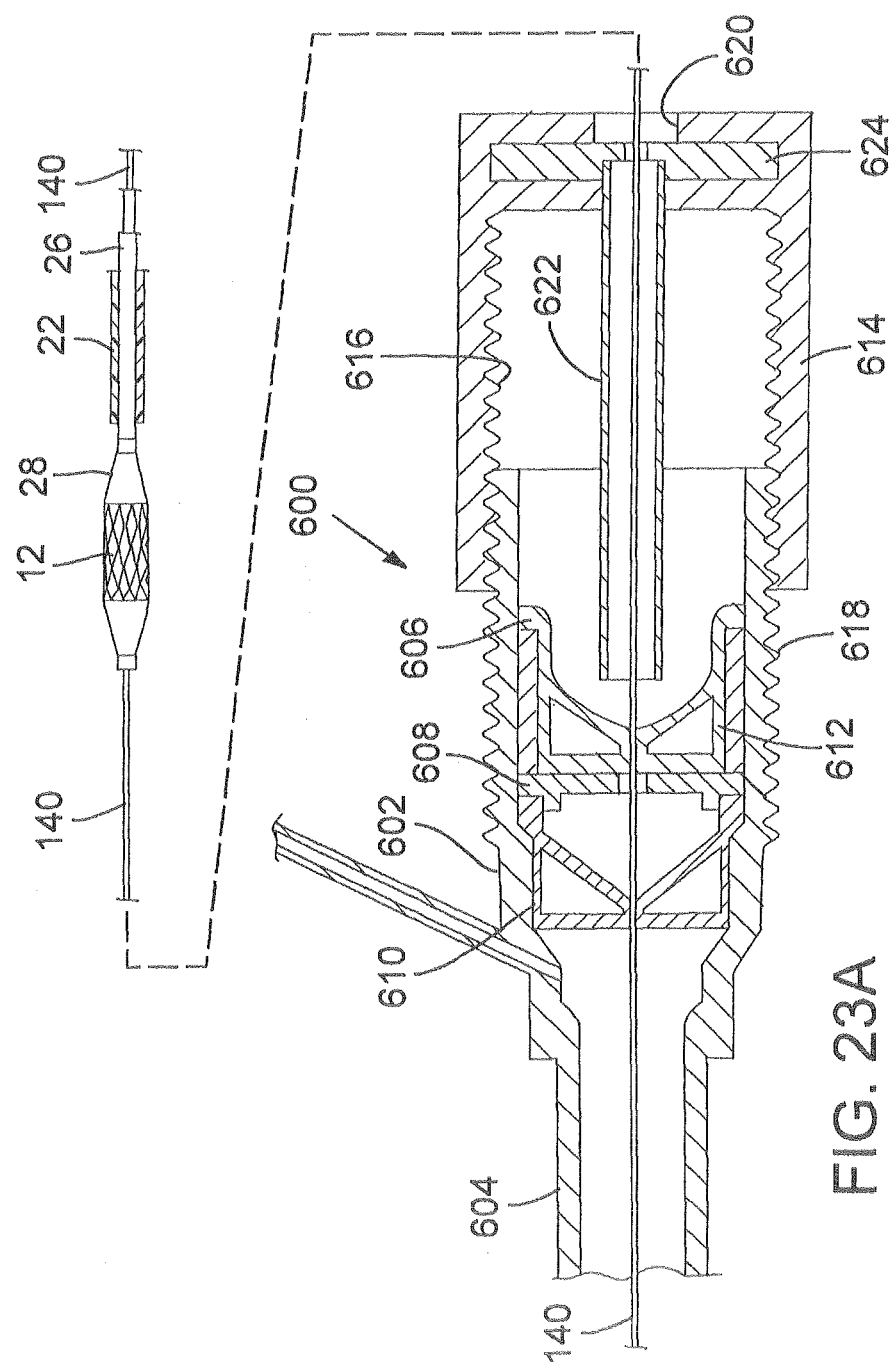
FIG. 23A shows a cross-sectional view of another embodiment of an introducer sheath and an exemplary delivery apparatus that can be introduced into a patient's vasculature via the sheath.
Figure 23B:
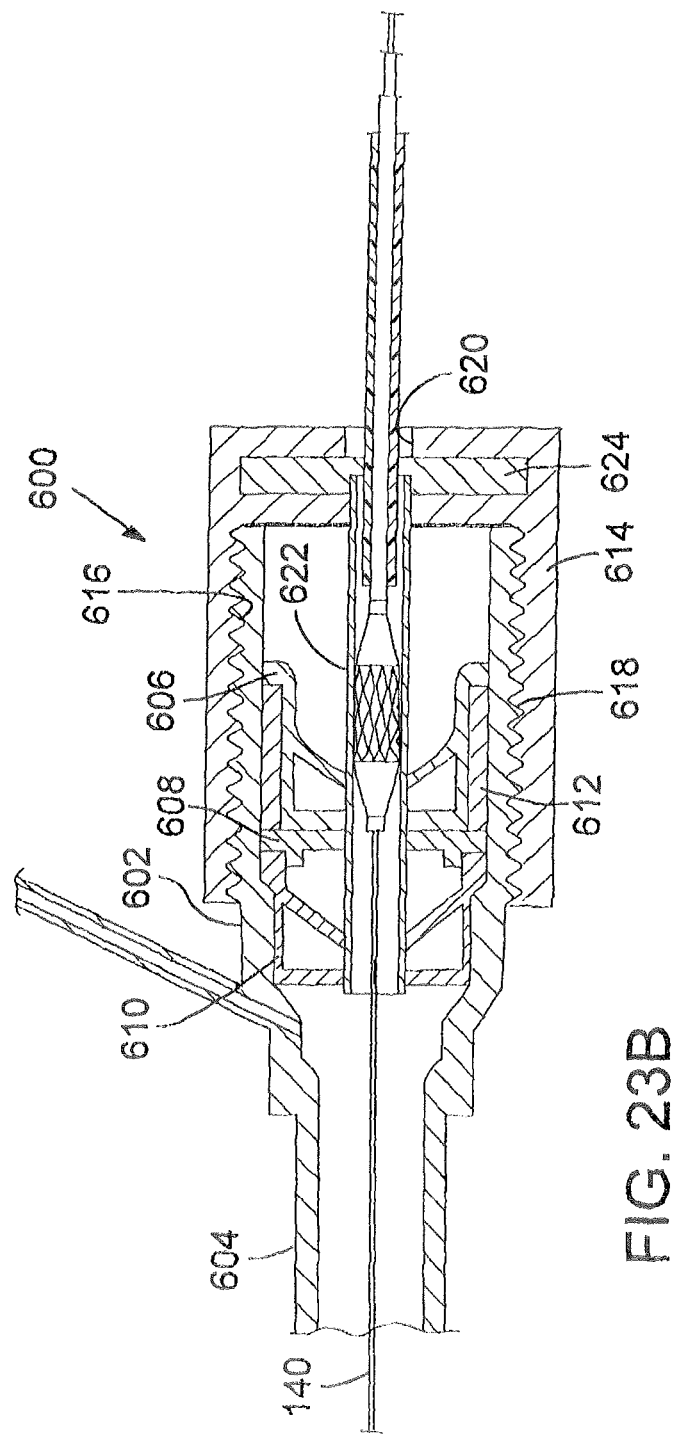
FIG. 23B is a cross-sectional view of the introducer sheath of FIG. 23A after insertion of the delivery apparatus into the sheath.

FIGS. 23A and 23B show an embodiment of an improved introducer sheath, indicated at 600, that can be used to facilitate insertion of a delivery apparatus into a body vessel. The introducer sheath 600 is particularly suited for use with a delivery apparatus that is used to implant a prosthetic valve, such as the embodiments of delivery apparatus described herein. The introducer sheath 600 also can be used to introduce other types of delivery apparatus for placing various types of intraluminal devices (e.g., stents, stented grafts, etc.) into many types of vascular and nonvascular body lumens (e.g., veins, arteries, esophagus, ducts of the biliary tree, intestine, urethra, fallopian tube, other endocrine or exocrine ducts, etc.). The example illustrated in FIG. 23A shows the distal end portion of a delivery apparatus used to implant a prosthetic valve 12. The delivery apparatus comprises a balloon catheter and a guide catheter. The balloon catheter comprises a shaft 26 and a balloon 28 mounted on the distal end portion of the shaft. The guide catheter comprises a shaft 22 extending over the balloon catheter shaft 26. The remaining portions of the balloon catheter and the guide catheter can be constructed according to the embodiment shown in FIGS. 1-8.

A conventional introducer sheath typically requires a tubular loader to be inserted through the seals in the sheath housing to provide an unobstructed path for a valve mounted on a balloon catheter. The loader extends from the proximal end of the introducer sheath, thereby increasing its working length, and decreasing the available working length of a delivery apparatus that can be inserted into the body. The introducer sheath 600 includes a integrated loader tube housed in the sheath housing to reduce the working length of the sheathe and therefore increase the available working length of a delivery apparatus that can be inserted into the body.

For example, the illustrated sheath 600 includes a seal housing 602 and a tubular sleeve 604 extending distally from the housing. The seal housing 602 houses one or more sealing valves, such as a cross-slit valve 606, a disc valve 608, and a hemostatic valve 610 as shown in the illustrated embodiment. The valves desirably are fabricated from a resilient biocompatible material, such as polyisoprene, although similar biocompatible materials also can be used. The valves 606, 608, 610 are further shown and described in U.S. Pat. No. 6,379,372, which is incorporated herein by reference. A spacer 612 can be interposed between the disc valve 608 and the cross-slit valve 606.

Coupled to the proximal end of the seal housing is an end piece 614 adapted to move longitudinally along the length of the seal housing. In the illustrated embodiment, the end piece has a tubular body formed with internal threads 616 that engage external threads 618 formed on the outer surface of the seal housing 602. Thus, rotation of the end piece 614 moves the same inwardly and outwardly relative to the seal housing. The end piece 614 has a central opening 620 and an elongated loader tube 622 fixedly secured to the proximal end portion of the end piece and extending distally therefrom. The opening 620 and the loader tube 622 are dimensioned to permit passage of the valve 12 (or other prosthesis) mounted on the delivery apparatus. The end piece 614 also houses a seal 624 having a central opening aligned with the opening 620. The seal 624 sealingly engages the outer surface of the delivery apparatus when it is inserted into the introducer sheath 600.

As noted above, the end piece 614 can be adjusted inwardly and outwardly relative to the seal housing 602. Adjusting the end piece 614 from the extended position shown in FIG. 23A to the retracted position shown in FIG. 23B moves the loader tube 622 through the seals 606, 608, 610 to provide an unobstructed path for the valve 12 to pass through the introducer sheath. Because the loader tube does not extend behind the end piece, as in a conventional introducer sheath, the loader tube does not decrease the available working length of the delivery apparatus that can be inserted into the vasculature.

In use, the introducer sheath 600 in the extended position shown in FIG. 23A can be placed on a previously inserted guide wire 140 and advanced thereon until the sleeve 604 extends into a body vessel a desired distance. The delivery apparatus can then be inserted through the opening 620 to position the valve 12 in the loader tube 622 with the seal 624 forming a fluid tight seal around the guide catheter shaft 22. Subsequently, the end piece 614 is rotated to slide the loader tube 622 through the valves 606, 608, 610 (FIG. 23B), thus placing the delivery apparatus in communication with the lumen of the sleeve 604 and the body vessel in which the sleeve is inserted. Advantageously, this approach simplifies the loading process and reduces the number of steps and parts required to load the valve into the sheath.

In an alternative embodiment of the introducer sheath 600, the seal housing 602 can have internal threads that engage external threads on the end piece 614. The end piece can be rotated to adjust the position of the loader tube 622 as previously described. In addition, the pitch of the threads on the seal housing and the end piece can be varied to vary the amount of rotational movement required to extend the loader through the sealing valves. In another embodiment, the end piece 614 can be slidingly positionable along the length of the seal housing by pushing and pulling the end piece without rotating the same.

FIGS. 24A and 24B show another embodiment of a nose catheter, indicated at 700, that can be used in the delivery apparatus 10 (FIG. 1). The nose catheter 700 includes a nose piece 702 and a nose catheter shaft 704. The nose piece 702 has a distal end 706 connected to the nose catheter shaft 704 and a proximal end connected to the distal end of a balloon catheter shaft 26. The nose piece 702 comprises a balloon or similar structure formed from a thin, flexible material, such as nylon or PET, capable of assuming an inverted shape covering a valve 12 and a balloon 28 or portions thereof when the nose piece 702 is urged against the balloon 28. For example, the nose piece 702 can have a structure similar to the balloon 28.

The nose catheter shaft 704 is slidable relative to the balloon catheter shaft 26, although the proximal end of the nose piece 702 is connected to the balloon catheter shaft. Hence, as the nose catheter shaft 704 is moved proximally relative to the balloon catheter shaft 26 (in the direction of arrow 710) from a first, extended position (FIG. 24B) toward a second, retracted position (FIG. 24A), the nose piece 702 is urged against the distal end of the balloon catheter shaft 26, causing the nose piece 702 to assume an inverted position covering a portion of the outer surface of the balloon 28 and the valve 12. Similarly, it can be seen that moving the balloon catheter shaft distally relative to the nose catheter shaft from the extended position shown in FIG. 24B also is effective to cause the nose piece to assume an inverted position over the balloon and the valve.

In use, the nose piece 702 is initially placed in the inverted position shown in FIG. 24A to provide a smooth tracking profile during delivery of the valve through the patient's vasculature. At or near the implantation site, the nose catheter shaft 704 is moved distally relative to the balloon catheter shaft 20 (in the direction of arrow 712) to uncover the valve 12 and the balloon 28 for subsequent deployment of the valve. Desirably, although not necessarily, the nose piece 702 can be partially inflated so that it can more readily assume the inverted position shown in FIG. 24A. In this regard, the lumen of the nose catheter shaft 704 can be fluidly connected to a fluid source for partially inflating the nose piece 702, similar to the way the balloon catheter shaft is used to deliver a fluid to the balloon 28.

Figure 25A:
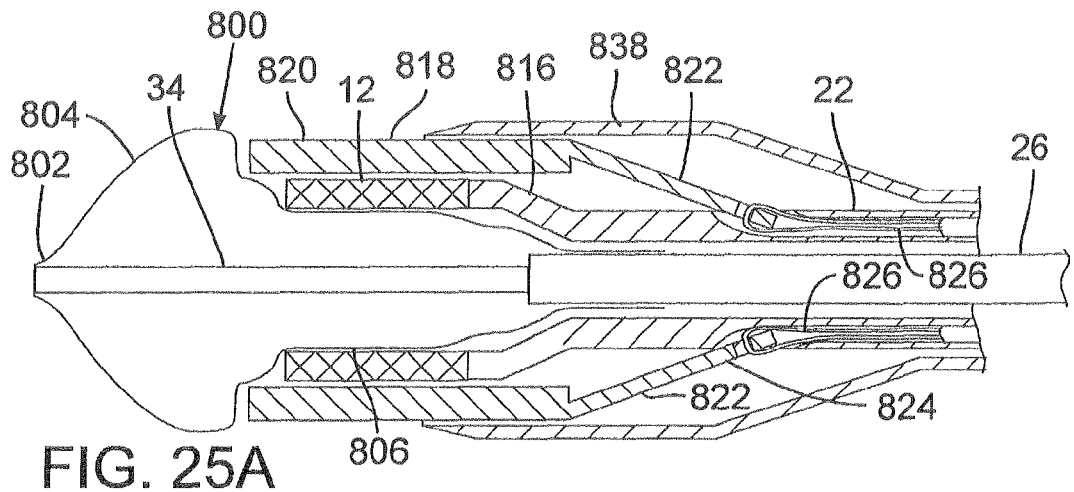
FIGS. 25A-25E schematically illustrate another embodiment of a delivery apparatus.
Figure 25D:
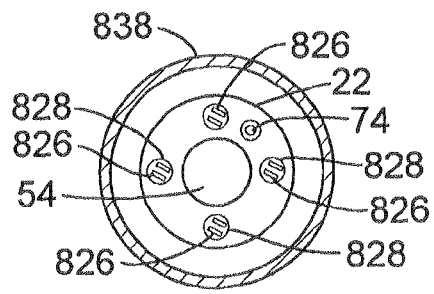
Figure 25C:
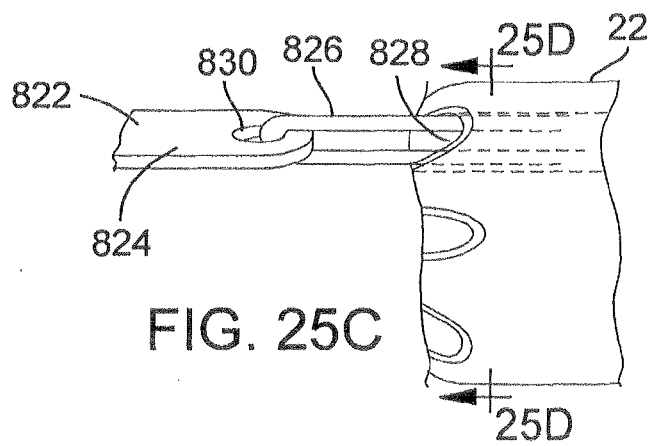

FIG. 25A shows the distal end portion of a modification of the delivery apparatus 10. The delivery apparatus in this embodiment includes a stepped balloon 800 mounted on the distal end portion of the balloon catheter shaft 26 and inner shaft 34. As shown in FIG. 25B, the illustrated balloon 800 includes a first slender portion 802, a first conical portion 804, a main cylindrical portion 806, a second conical portion 808, a second cylindrical portion 810, a third conical portion 812, and a second slender portion 814. A valve 12 (FIG. 25A) can be mounted in a crimped state on the main cylindrical portion 806. The stepped balloon 800 is further described in detail in co-pending U.S. application Ser. No. 11/252,657 (the '657 application) (published as U.S. Patent Application Publication No. 2007/0088431), which is incorporated herein by reference.

As shown in FIG. 25A, the delivery apparatus includes a guide catheter comprising a guide catheter shaft 22 having an enlarged end portion 816 that abuts the proximal end of the valve 12. The guide catheter further includes a retractable cover 818 that extends over and covers the valve 12. The cover 818 is operable to slide longitudinally relative to the valve and the distal end of the guide catheter shaft 22 to uncover the valve for deployment inside a body vessel. Portions 802, 804 of the balloon 800 extend from the distal end of the cover 818 and can be partially inflated to provide a transition member between the distal end of the balloon catheter and the cover 818, thereby facilitating tracking through the patient's vasculature, much like nose piece 32 (FIG. 1). The end of the balloon extending from the cover 818 also can be used as a dilator to dilate stenotic leaflets of a native heart valve or other portions of the patient's vasculature prior to deploying the valve at the desired implantation site, as further described in the '657 application.

As further shown in FIG. 25A, the cover 818 in the illustrated embodiment has a cylindrical distal end portion 820 that extends over the valve 12 and a plurality of circumferentially spaced fingers 822 extending proximally from the proximal end of the cylindrical distal end portion 820. The proximal end portion of each finger 822 is connected to a pull wire 826 that extends through a respective lumen in the guide catheter shaft 22. As shown in FIG. 25C, each pull wire 826 extends distally from a respective lumen 828, through an opening 830 in the proximal end portion 824 of a respective finger 822, and back into the lumen 828. The guide catheter can further include a flexible outer cover 838 extending over the portions of the pull wires 826 extending from the shaft 22 to prevent the wires from contacting the inner walls of the vasculature. The cover 838 can be fixedly secured to the outer surface of the shaft 22, such as with a suitable adhesive. Alternatively, the cover 838 can be adapted to slide longitudinally relative to the shaft 22.

The cover 818 in the illustrated example has four fingers 822, each of which is connected to a pull wire 826 that extends through a respective lumen 828. As shown in FIG. 25D, the lumens 828 can be equally spaced around a central lumen 54 of the shaft 22. The shaft 22 also can include another lumen for receiving a pull wire 74 for adjusting the curvature of the guide catheter, as described above. The pull wires 826 extend the length of the guide catheter shaft 22 and are operatively connected to an adjustment mechanism at the proximal end of the shaft to permit manual adjustment of the pull wires 826, and therefore the cover 818.

Figure 25E:
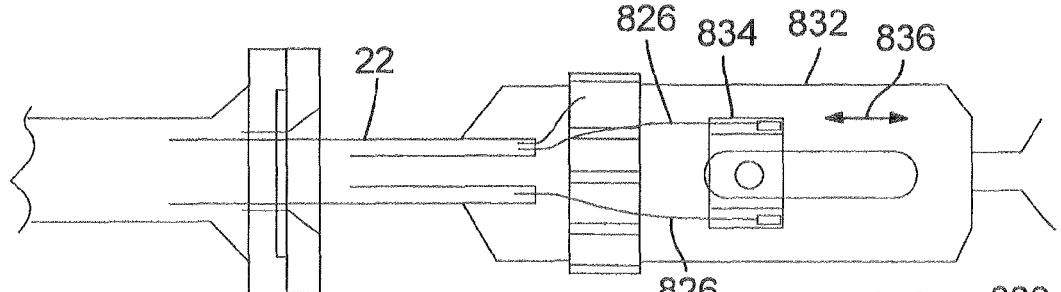
Figure 25B:
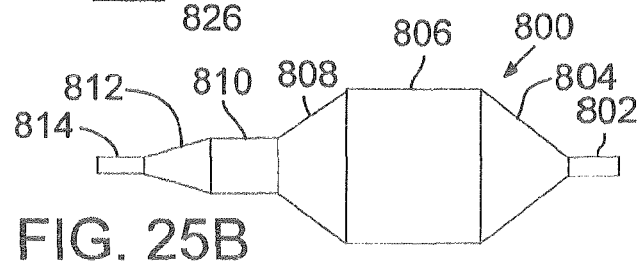
Figure 26A:
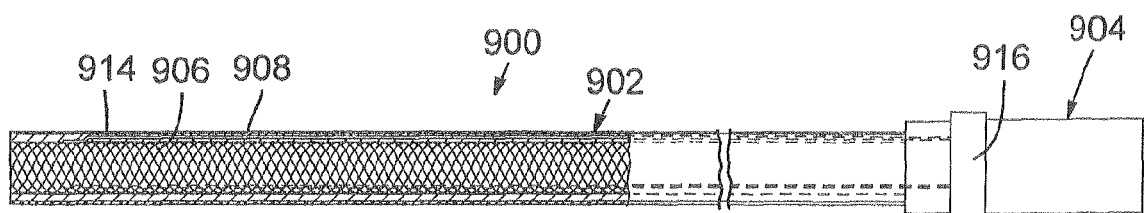
FIGS. 26A-26E schematically illustrate another embodiment of an introducer sheath.
Figure 26B:
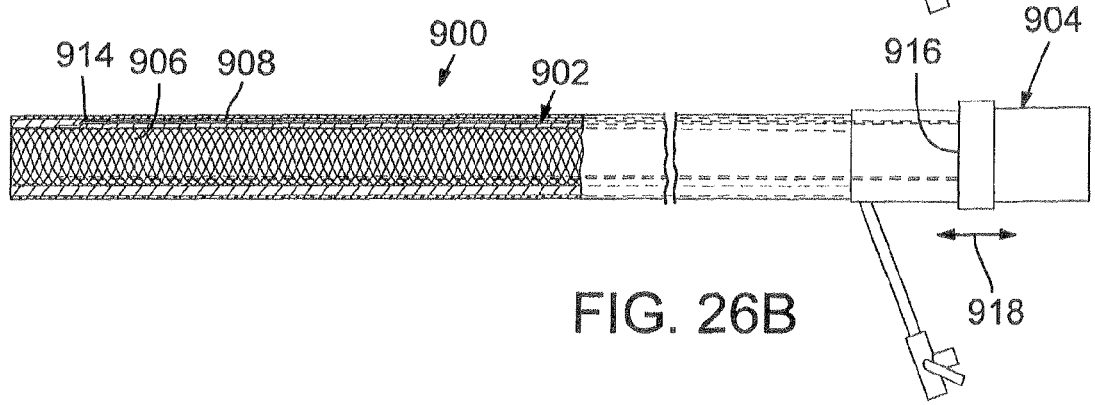
Figure 26C:
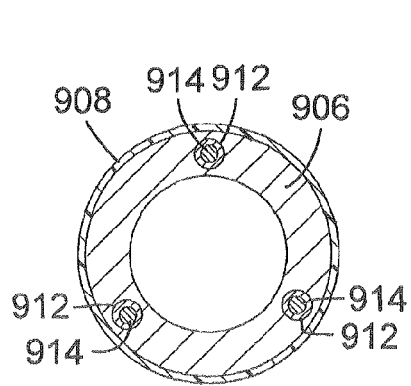
Figure 26D:
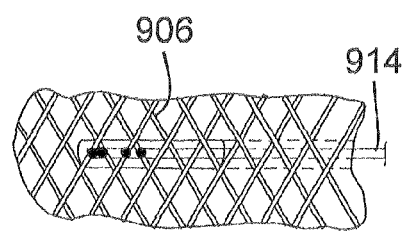
Figure 26E:
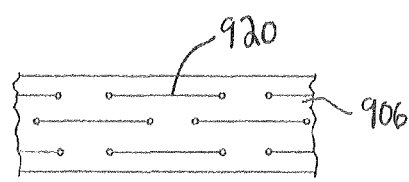

FIG. 25E is a schematic illustration of a handle portion 832 connected to the proximal end of the guide catheter shaft. The handle potion 832 can have a construction similar to the handle portion 20 (described above and shown in FIGS. 3A-3B) except that the former can include an additional adjustment mechanism 834 connected to the pull wires 826. The adjustment mechanism 834 can be moved fore and aft (in the directions of double-headed arrow 836) by the operator to move the pull wires 826. The pull wires 826 desirably exhibit sufficient rigidity to apply a pushing force to the cover 818 in the distal direction without buckling. The pull wires can be, for example, 0.006 inch×0.012 inch Nitinol ribbon wire. In this manner, the cover 818 can be retracted in the proximal direction relative to the valve, and if necessary, moved in the distal direction, such as to retrieve the valve back into the cover 818, by operation of the adjustment mechanism 834. Further details of an adjustment mechanism that can be used to produce movement of the pull wires in the distal and proximal directions is described in detail in the '657 application.

When the valve is advanced to the implantation site inside the body, the cover 818 is retracted by operation of the adjustment mechanism to uncover the valve. As the cover 818 is retracted (relative to the shaft 22 and the outer cover 838), the distal end of the shaft end portion 816 abuts against the valve to prevent inadvertent movement of valve's position on the balloon 800. Thereafter, the balloon catheter can be advanced distally relative to the guide catheter to advance the balloon 800 a sufficient distance from the cover 838 and the shaft end portion 816 to permit full inflation of the balloon for deploying the valve 12. The valve 12 can be a balloon-expandable valve that is deployed by the balloon, or alternatively, the valve 12 can be a self-expanding valve that radially expands when advanced from the cover 818. In the latter case, the balloon 800 can be used to further expand the valve to ensure tight engagement with the orifice of the native valve.

In an alternative embodiment, the shaft distal end portion 816 can be configured to provide a releasable attachment to the valve 12, such as described in detail in the '657 application. In this manner, the guide catheter can be moved fore and aft to adjust the position of the valve in the body vessel as the valve is being deployed. Prior to deployment (or after partial deployment, or expansion, of the valve), control of valve positioning can be achieved by the operator pushing, pulling, or twisting the guide catheter. Once the operator is satisfied with the position of the valve, the valve can be fully deployed and the valve is detached from the distal end of the guide catheter shaft.

FIGS. 25A-25E illustrate another embodiment of an introducer sheath, indicated at 900, that can be used to facilitate the introduction of a delivery apparatus into a blood vessel. The introducer sheath 900 has an expandable, elongated sleeve 902 that can be radially expanded from a first diameter (FIG. 25A) to a second, larger diameter (FIG. 25B) to facilitate insertion of the largest portion the delivery apparatus (the portion on which the valve or other prosthetic device is mounted). The sheath 900 further includes a handle portion 904 connected to the proximal end of the sleeve 902. The sleeve 902 includes an inner layer 906 and an outer layer 908. The inner layer 906 can be a braided polymeric layer made from a suitable material such as, peek, nylon, or polypropylene. The outer layer 908 can be formed from urethane or another suitable material. The outer surface of the outer layer 908 can be provided with a hydrophilic coating. The handle portion 904 can house one or more sealing valves configured to sealingly engage the outer surface of a delivery apparatus inserted through the sheath, as previously described.

As shown in FIG. 25C, the sleeve 902 can be formed with a main lumen 910 sized to permit passage of a delivery apparatus and one or more inner conduits 912 defining side lumens spaced around the main lumen 910. Extending through each side lumen is a respective pull wire 914. The proximal end of each pull wire 914 is connected to an adjustment mechanism 916 on the handle portion 904. The distal end of each pull wire 914 is fixedly secured to the distal end portion of the sleeve 902. For example, as shown in FIG. 25D, each pull wire 914 can extend outwardly from the distal end of a respective lumen and can be welded to the inner layer 906 adjacent the distal end of the sleeve.

The adjustment mechanism 916 is configured to permit manual adjustment of the diameter of the sleeve 902 between a first diameter (FIG. 25A) and a second, larger diameter (FIG. 25B). In the illustrated embodiment, for example, the adjustment mechanism can move longitudinally relative to the handle portion 904, in the directions indicated by double-headed arrow 918. Moving the adjustment mechanism in the proximal direction (away from the sleeve 902) is effective to pull the pull wires 914 in the same direction, which causes the sleeve 902 to radially expand and to shorten in length. Moving the adjustment mechanism 914 in the distal direction (toward the sleeve) releases tension on the pull wires 914 to permit the sleeve 902 to radially contract and elongate under its own resiliency. In particular embodiments, the sleeve 902 has an outer diameter of about 18 F in its contracted state and can expand to an outer diameter of about 28 F.

In use, the sleeve 902 can be inserted into a blood vessel as previously described. As a delivery apparatus (e.g., delivery apparatus 10) is inserted through the sleeve 902, the sleeve 902 can be radially expanded to allow a prosthetic valve (e.g., valve 12) or other prosthetic device mounted on the delivery apparatus to easily pass through the sleeve 902. Once the prosthetic valve is inserted into the blood vessel, the sleeve 902 can be reduced in diameter to minimize occlusion of the vessel.

In an alternative embodiment, as depicted in FIG. 25E, the inner layer 906 can be a laser cut tube rather than a braided layer. The tube can be formed with a plurality of longitudinally extending cuts or slits 920 that allow the tube to radially expand and contract.

The various embodiments of the delivery apparatus disclosed herein can be used for implanting prosthetic devices other than prosthetic heart valves into the body. For example, the delivery apparatus can be used to deliver and deploy various types of intraluminal devices (e.g., stents, stented grafts, etc.) into many types of vascular and non-vascular body lumens (e.g., veins, arteries, esophagus, ducts of the biliary tree, intestine, urethra, fallopian tube, other endocrine or exocrine ducts, etc.). In one specific example, the delivery apparatus can be used to implant a balloon-expandable stent into a coronary artery (or other blood vessels) to maintain the patency of the vessel lumen.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An apparatus for delivering a prosthetic valve through the vasculature of a patient comprising:

a crimped prosthetic valve comprising a stent portion supporting a valve structure;

a balloon catheter comprising an elongated shaft, a balloon connected to a distal end portion of the shaft, the balloon being adapted to carry the prosthetic valve in a crimped state and being inflatable to deploy the prosthetic valve at an implantation site in the patient's body, the elongate shaft of the balloon catheter further comprising a distal end portion extending distally of the balloon and an annular tapered wedge secured to the distal end portion of the elongate shaft, the tapered wedge distal of the balloon, the tapered wedge having a narrower distal end and a wider proximal end, the tapered wedge dimensioned to expand the crimped prosthetic valve when the prosthetic valve is urged thereagainst, the crimped prosthetic valve disposed on the distal end portion of the balloon catheter distal of the tapered wedge;

a guide catheter comprising an elongated shaft extending over the balloon catheter shaft, the shaft of the guide catheter comprising a selectively steerable section for facilitating advancement through the vasculature of the patient, the guide catheter further comprising an adjustment mechanism operatively coupled to the steerable section, the adjustment mechanism being configured to adjust the curvature of the steerable section and the portion of the balloon catheter shaft extending through the steerable section, movement of the adjustment mechanism causing a substantially 1:1 movement of the steerable section;

a nose catheter comprising an elongated shaft extending through the balloon catheter shaft and a nose piece connected to a distal end of the nose catheter shaft, the nose piece having a shoulder dimensioned to engage a distal end of the crimped prosthetic valve during delivery of the prosthetic valve, the nose piece having an outer layer and an inner layer, the outer layer softer than the inner layer; and a cover secured to and extending distally from the distal end of the guide catheter, the cover and nose piece dimensioned to cover the crimped prosthetic valve and the balloon, wherein the balloon catheter, the guide catheter, and the nose catheter are configured to move longitudinally relative to each other such that the cover may be advanced relative to the prosthetic valve for exposing the prosthetic valve, the balloon catheter may be advanced relative to the nose catheter to push the crimped prosthetic valve over the tapered wedge and onto the balloon, and the balloon catheter may be advanced relative to the guide catheter for deploying the prosthetic valve at a treatment site.

2. The apparatus of claim 1, wherein the cover is adapted to extend over the valve during delivery.

3. The apparatus of claim 1, wherein the nose piece and the cover can be positioned to completely enclose the crimped prosthetic valve and the balloon in its deflated state during delivery.

4. The apparatus of claim 1, further comprising a locking mechanism configured to retain the balloon catheter at selected longitudinal positions relative to the guide catheter.

5. The apparatus of claim 4, wherein the balloon catheter shaft has a proximal end portion formed with a plurality of longitudinally spaced-apart grooves and the locking mechanism comprises a latch member connected to the guide catheter, the latch member being engageable with the grooves and adapted to retain the balloon catheter from moving longitudinally relative to the guide catheter when the latch member is aligned with and engages a selected groove.

6. The apparatus of claim 5, wherein the latch member and the grooves permits rotational movement of the balloon catheter relative to the guide catheter when the latch member engages one of the grooves.

7. The apparatus of claim 1, further comprising a locking mechanism configured to retain the nose catheter at selected longitudinal positions relative to the balloon catheter.

8. The apparatus of claim 1, wherein the nose catheter shaft has a lumen adapted to receive a guide wire so that the nose catheter, the balloon catheter, and the guide catheter can be advanced together over the guide wire.

9. The apparatus of claim 1, wherein the nose piece is adapted to completely cover the valve during delivery.

10. The apparatus of claim 9, wherein the nose piece is adapted to substantially cover the balloon during delivery.

11. The apparatus of claim 1, wherein the adjustment mechanism comprises a pivotable lever and a pull wire having a proximal end portion coupled to the lever and a distal end portion fixedly secured at a distal end portion of the steerable section such that pivoting of the lever is effective to apply a pulling force on the pull wire, which in turn causes the steerable section to bend.

12. The apparatus of claim 1, wherein the cover is dimensioned to abut against a proximal end surface of the nose piece.

13. The apparatus of claim 1, wherein the nose piece comprises a flexible material.

14. An apparatus for delivering a prosthetic valve through a vasculature of a patient, the apparatus comprising:
   a balloon catheter comprising an elongated shaft, a balloon disposed at a distal end portion of the elongate shaft, the balloon proximal of a distal end of the elongate shaft thereby defining a distal end portion of the elongate shaft distal of the balloon, the balloon inflatable to expand a prosthetic valve disposed thereon, the distal end of the elongate shaft dimensioned to carry a crimped prosthetic valve thereon;
   a tapered wedge secured distal of the balloon on the distal end portion of the elongate shaft, the tapered wedge dimensioned to expand the crimped prosthetic valve when the prosthetic valve is pushed thereagainst;
   a guide catheter comprising an elongate shaft extending over the balloon catheter shaft, a distal portion of the guide catheter selectively steerable; and
   a nose piece disposed at a distal end of a nose catheter, the nose catheter comprising an elongate shaft extending through the balloon catheter shaft;
   wherein the balloon catheter, the guide catheter, and the nose catheter are longitudinally slidable relative to each other such that the balloon catheter is advanceable relative to the nose catheter for pushing a crimped prosthetic valve disposed on the distal end portion of the elongate shaft of the balloon catheter over the tapered wedge and onto the balloon, and the balloon catheter is advanceable relative to the guide catheter for deploying the prosthetic valve at a treatment site.

15. The apparatus of claim 14, wherein the nose piece is dimensioned to cover the tapered wedge.

16. The apparatus of claim 14, further comprising a cover secured to and extending distally from a distal end of the guide catheter, the cover and nose piece dimensioned to cover the crimped prosthetic valve and the balloon.

17. The apparatus of claim 14, further comprising a crimped prosthetic valve disposed on the distal end portion of the elongate shaft of the balloon catheter.

18. The apparatus of claim 17, wherein the prosthetic valve comprises a stent portion supporting a valve structure.

19. The apparatus of claim 14, further comprising an adjustment mechanism coupled to the steerable section of the guide catheter, the adjustment mechanism operable to adjust a curvature of the steerable section.

20. The apparatus of claim 14, wherein the nose piece comprises an outer layer and an inner layer, the outer layer softer than the inner layer.

21. The apparatus of claim 14, wherein a longitudinal position of the balloon catheter is lockable relative to the guide catheter.

22. The apparatus of claim 14, wherein a longitudinal position of the nose catheter is lockable relative to the balloon catheter.

23. The apparatus of claim 14, wherein the nose piece has a shoulder dimensioned to engage a distal end of the crimped prosthetic valve disposed on the distal end portion of the elongate shaft of the balloon catheter.

* * * * *